(12) United States Patent
Vaillancourt et al.

(10) Patent No.: US 9,061,013 B2
(45) Date of Patent: Jun. 23, 2015

(54) ISOXAZOLINE DERIVATIVES AS ANTIPARASITIC AGENTS

(75) Inventors: Valerie A. Vaillancourt, Portage, MI (US); John A. Wendt, Mattawan, MI (US); Graham M. Kyne, Portage, MI (US); Sanjay Menon, Kalamazoo, MI (US)

(73) Assignee: Zoetis LLC, Florham Park, NJ (US)

( * ) Notice: Subject to any disclaimer, the term of this patent is extended or adjusted under 35 U.S.C. 154(b) by 91 days.

(21) Appl. No.: 14/005,943

(22) PCT Filed: Mar. 8, 2012

(86) PCT No.: PCT/IB2012/051086
§ 371 (c)(1),
(2), (4) Date: Sep. 18, 2013

(87) PCT Pub. No.: WO2012/127347
PCT Pub. Date: Sep. 27, 2012

(65) Prior Publication Data
US 2014/0011758 A1 Jan. 9, 2014

Related U.S. Application Data

(60) Provisional application No. 61/466,072, filed on Mar. 22, 2011.

(51) Int. Cl.
| | | |
|---|---|---|
| C07D 261/04 | (2006.01) | |
| C07D 413/10 | (2006.01) | |
| A01N 43/80 | (2006.01) | |
| A01N 55/00 | (2006.01) | |
| A61K 31/42 | (2006.01) | |
| A61K 45/06 | (2006.01) | |
| A61K 31/422 | (2006.01) | |

(52) U.S. Cl.
CPC ............ *A61K 31/422* (2013.01); *C07D 261/04* (2013.01); *C07D 413/10* (2013.01); *A01N 43/80* (2013.01); *A01N 55/00* (2013.01); *A61K 31/42* (2013.01); *A61K 45/06* (2013.01)

(58) Field of Classification Search
None
See application file for complete search history.

(56) References Cited

FOREIGN PATENT DOCUMENTS

| | | |
|---|---|---|
| WO | 2007/070606 | 6/2007 |
| WO | 2007/075459 | 7/2007 |
| WO | 2008/019760 | 2/2008 |
| WO | 2008/150393 | 12/2008 |
| WO | 2009/051956 | 4/2009 |
| WO | 2010/020522 | 2/2010 |
| WO | 2012/017359 | 2/2012 |

OTHER PUBLICATIONS

PCT International Search Report, PCT/IB2012/051086, mailed Aug. 5, 2012 (3 pages).

*Primary Examiner* — Kamal Saeed
(74) *Attorney, Agent, or Firm* — Paul M. Misiak

(57) ABSTRACT

This invention recites isoxazoline substituted derivatives of Formula (1) stereoisomers thereof, geometric isomers thereof, veterinarily acceptable salts 5 thereof, compositions thereof, and their use as a parasiticide in animals. The variables A, W, R 1a, R 1b, R 1c, R 2, R 3, R 5, and n are as described herein.

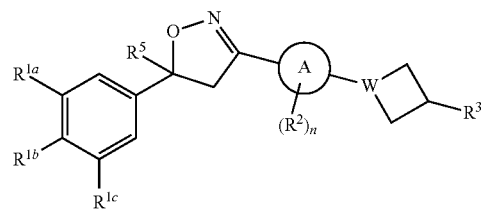

15 Claims, No Drawings

ISOXAZOLINE DERIVATIVES AS ANTIPARASITIC AGENTS

FIELD OF THE INVENTION

There is a need for improved antiparasitic agents for use with animals, and in particular there is a need for improved insecticides and acaricides. Furthermore there is a need for improved topical and oral products with convenient administration and which contain one or more of such antiparasitic agents which can be used to effectively treat ectoparasites, such as insects (e.g., fleas, lice, and flies) and acarids (e.g., mites and ticks). Such products would be particularly useful for the treatment of companion animals, such as cats, dogs, llamas, and horses, and livestock, such as cattle, bison, swine, sheep, and goats.

The compounds currently available for insecticidal and acaricidal treatment of animals do not always demonstrate good activity, good speed of action, or a long duration of action. Most treatments contain hazardous chemicals that can have serious consequences, including neurotoxicity and lethality from accidental ingestion. Persons applying these agents are generally advised to limit their exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance.

Isoxazoline derivatives have been disclosed in the art as having insecticidal and acaricidal activity. WO2007/075459, WO2008/019760, WO2008/150393, and WO2009/051956 disclose phenyl isoxazolines substituted with a 5- or 6-membered heterocycle. Despite the availability of effective, broad spectrum antiparasitic agents, there remains a need for a safer, convenient, efficacious, and environmentally friendly product that will overcome the ever-present threat of resistance development.

These citations do not exemplify any phenyl isoxazolines substituted with azetidine, nor does the prior art indicate that such compounds would be useful against a spectrum of parasitic species relevant to companion animals and livestock or against the range of parasitic morphological lifecycle stages.

The present invention overcomes one or more of the various disadvantages of, or improves upon, the properties of existing compounds. In particular the present invention develops new isoxazoline substituted phenyl azetidines which demonstrate such properties.

SUMMARY

The present invention provides Formula (1) compounds, stereoisomers thereof, which act as parasiticides, in particular, ectoparasiticides; therefore may be used to prevent, treat, repel, and control acarids and insect infection and infestation in animals. In addition, the invention contemplates the control and prevention of tick borne diseases, for example, Lyme disease, canine and bovine anaplasmosis, canine ehrlichiosis, canine rickettsiosis, canine and bovine babesiosis, epizootic bovine abortion, and theileriosis. Thus, according to the invention, there is provided a compound of Formula (1)

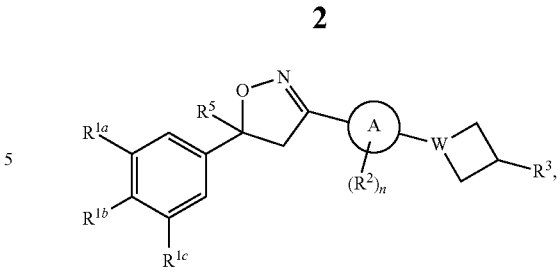

wherein

A is phenyl, naphthyl, or heteroaryl where said heteroaryl contains 1 to 4 heteroatoms each independently selected from N, O and S;

W is N or $CR^c$;

$R^{1a}$, $R^{1b}$, and $R^{1c}$ are each independently hydrogen, halo, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;

$R^2$ is halo, cyano, $C_1$-$C_6$alkyl, nitro, hydroxyl, —C(O)NH$_2$, $C_2$-$C_6$alkenyl, $C_2$-$C_6$alkynyl, or —OR;

$R^3$ is —C(X)NR$^a$R$^4$ or —NR$^a$C(X)R$^4$, where X is O, S, or NR$^6$;

$R^4$ is hydrogen, $C_1$-$C_6$alkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle; wherein said phenyl, heteroaryl, and heterocycle moieties are optionally substituted with one or more substituents selected from cyano, halo, hydroxyl, $C_1$-$C_6$alkoxy, $C_1$-$C_6$alkyl, and $C_1$-$C_6$haloalkoxy;

$R^5$ is cyano, $C_1$-$C_6$alkyl, $C_1$-$C_6$haloalkyl, —C(O)NH$_2$, $C_2$-$C_6$alkenyl, $C_2$-$C_6$alkynyl, $C_2$-$C_6$haloalkenyl, or $C_2$-$C_6$haloalkynyl;

$R^6$ is hydrogen, $C_1$-$C_6$alkyl, hydroxyl, cyano, nitro, $S(O)_p$R, or $C_1$-$C_6$alkoxy;

R and R' are each independently $C_1$-$C_6$alkyl or $C_3$-$C_6$cycloalkyl;

$R^a$ is hydrogen, $C_1$-$C_6$alkyl, $C_0$-$C_3$alkyl$C_3$-$C_6$cycloalkyl, C(O)R$^4$, or C(O)OR; wherein the alkyl and alkylcycloalkyl moiety is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each of which may be optionally substituted with at least one halo;

$R^c$ is halo, hydroxyl, cyano, $C_1$-$C_5$alkyl, or $C_1$-$C_5$haloalkyl;

each of R, $R^2$, $R^3$, and $R^4$ $C_1$-$C_6$alkyl or $C_0$-$C_3$alkyl$C_3$-$C_6$cycloalkyl can be optionally and independently substituted by one or more substituents selected from cyano, halo, hydroxyl, oxo, $C_1$-$C_6$alkoxy, $C_1$-$C_6$alkyl, hydroxy$C_1$-$C_6$alkyl-, and $C_1$-$C_6$haloalkoxy, and wherein $R^4$ $C_1$-$C_6$alkyl and $C_0$-$C_3$alkyl$C_3$-$C_6$cycloalkyl can be further optionally substituted by —S(O)$_p$R$^b$, —NR$^a$R$^b$, —NR$^a$C(O)R$^b$, —SC(O)R', or —C(O)NR$^a$R$^b$;

n is the integer 0, 1, or 2, and when n is 2, each $R^2$ may be identical or different from each other; and p is the integer 0, 1, or 2;

stereoisomers thereof, geometric isomers thereof, and veterinarily acceptable salts thereof.

In another aspect of the invention, A is phenyl, naphthyl, pyridinyl, pyrimidinyl, pyrazolyl, imidazolyl pyrrolyl, furanyl, thiophenyl, triazolyl, tetrazolyl, thiazolyl, isoxazolyl, oxazolyl, oxadiazolyl, thiadiazolyl, pyridazinyl, pyrazinyl, benzofuranyl, benzothiophenyl, indolyl, benzimidazolyl, indazolyl, benzotriazolyl, thieno[2,3-c]pyridine, thieno[3,2-b]pyridine, and benzo[1,2,5]thiadiazole. In yet another aspect of the invention, A is phenyl, naphthyl, pyridinyl, pyrimidinyl, pyrazolyl, triazolyl, tetrazolyl, thiazolyl, isoxazolyl, benzofuranyl, benzothiophenyl, indolyl, and benzo[1,2,5]thiadiazole. In yet another aspect of the invention, A is phenyl, naphthyl, pyridinyl, pyrazolyl, triazolyl, isoxazolyl, benzofuranyl, and benzo[1,2,5]thiadiazole. In yet another aspect of the invention, A is phenyl, naphthyl, pyridinyl, pyrazolyl, and benzo[1,2,5]thiadiazole. In another aspect of the invention, A is phenyl, naphthyl, or benzo[1,2,5]thiadiazole. In another aspect of the invention A is phenyl. In another aspect of the invention, A is naphthyl. In yet another aspect of the invention, A is benzo[1,2,5]thiadiazole. In yet another aspect of the invention, A is pyridinyl.

In another aspect of the invention are compounds of Formula (1) where W is N. In another aspect of the invention are compounds of Formula (1) where W is N having Formula (2), (3), (4), (5), or (6), (2)

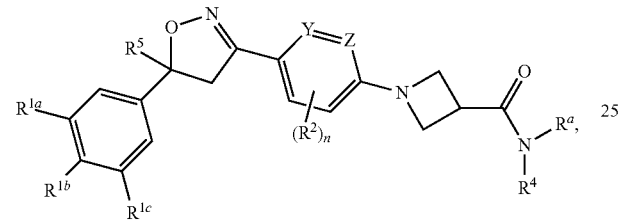

(3)

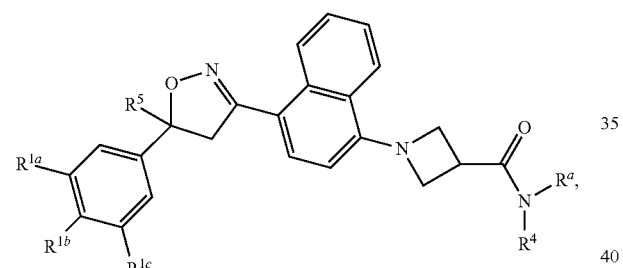

(4)

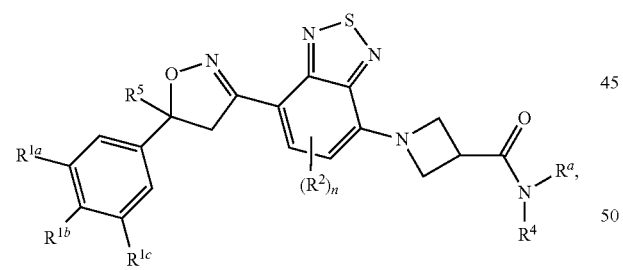

(5)

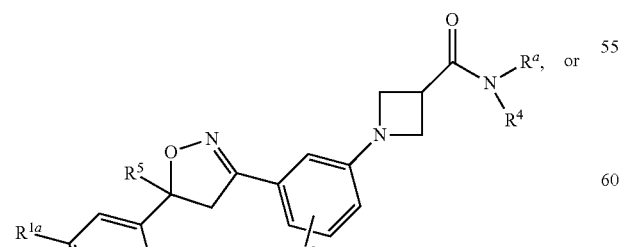

(6)

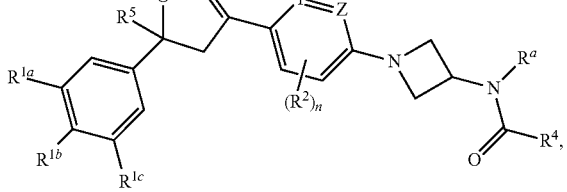

where Y and Z are both carbon, Y is carbon and Z is nitrogen, or Y is nitrogen and Z is carbon, stereoisomers thereof, and veterinarily acceptable salts thereof.

In yet another aspect of the invention are compounds of Formula (1) where W is N having Formula (2a), (2b), (2c), (2d), (2e), (2f), (3a), (4a), (4b), (5a), (5b), (6a), (6b), (6c), (6d), (6e), or (6f), (2a)

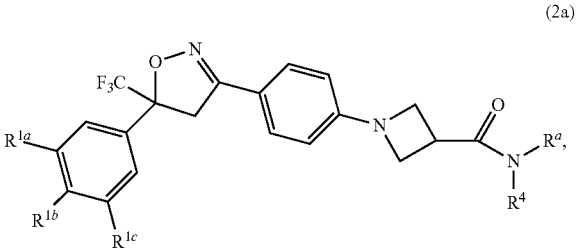

(2b)

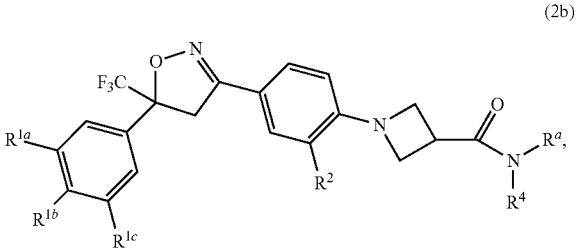

(2c)

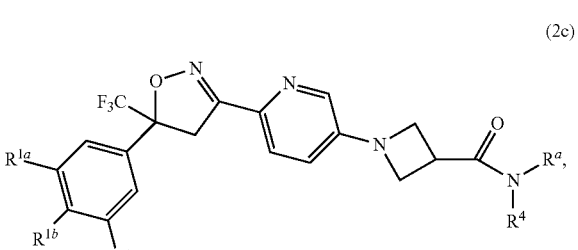

(2d)

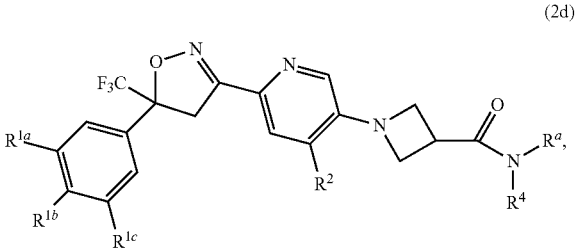

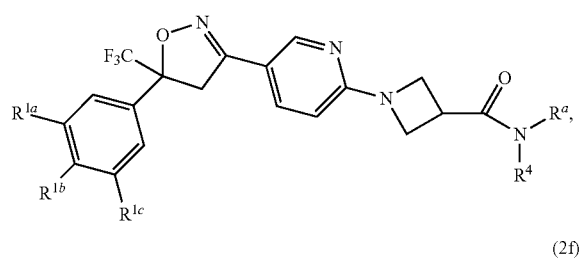
(2e)
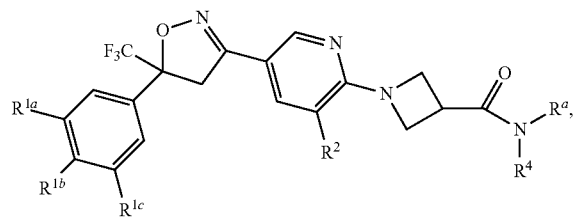
(2f)
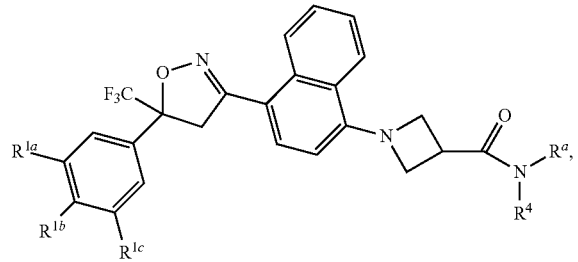
(3a)
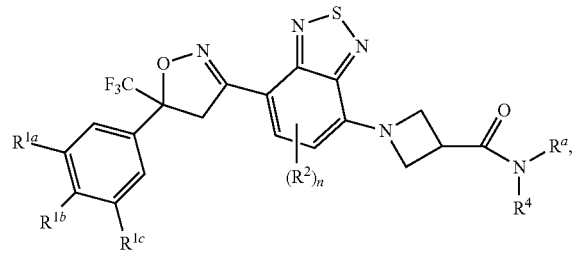
(4a)
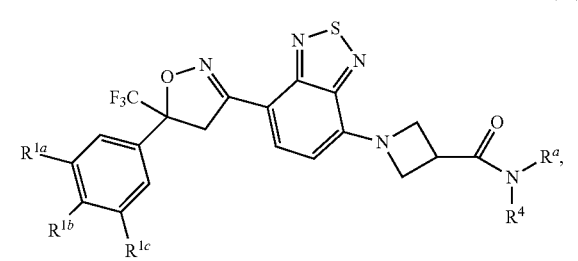
(4b)
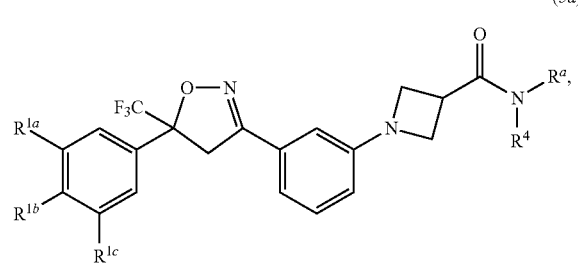
(5a)
(5b)
(6a)
(6b)
(6c)
(6d)
(6e)
or

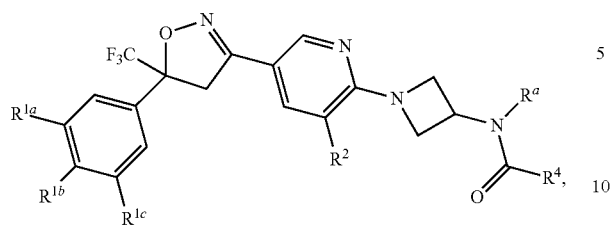

(6f)

stereoisomers thereof, and veterinarily acceptable salts thereof.

In another aspect of the invention are compounds of Formula (1) where W is $CR^c$. In another aspect of the invention are compounds of Formula (1) where W is $CR^c$ having Formula (7), (8), (9), (10), or (11),

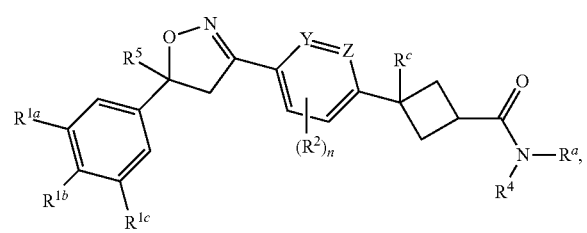

(7)

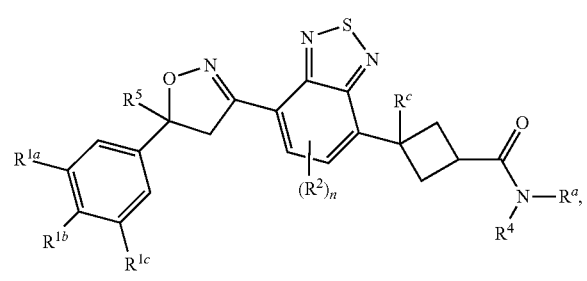

(8)

(9)

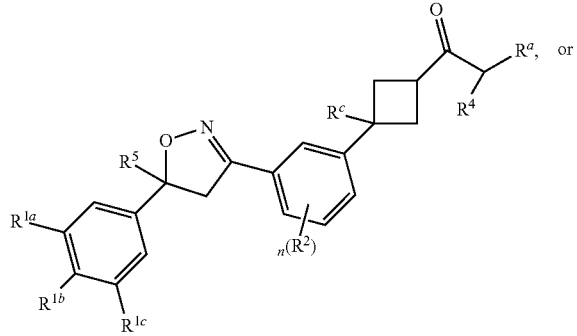

(10)

(11)

wherein Y and Z are both carbon, Y is carbon and Z is nitrogen, or Y is nitrogen and Z is carbon, stereoisomers thereof, geometric isomers thereof, and veterinarily acceptable salts thereof.

In yet another aspect of the invention are compounds of Formula (1) where W is $CR^c$ having Formula (7a), (7b), (7c), (7d), (7e), (7f), (8a), (9a), (10a), (11a), (11b), (11c), (11d), (11e), or (11f),

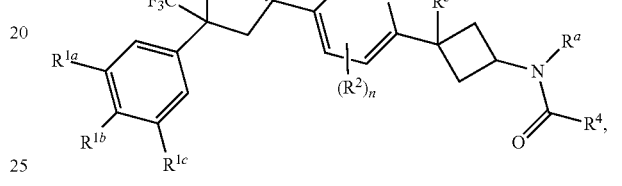

(7a)

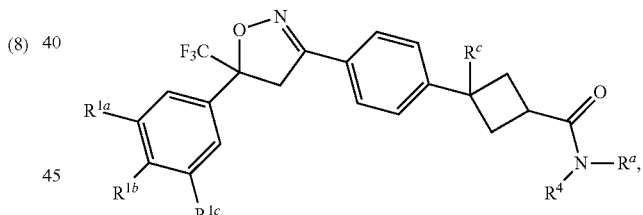

(7b)

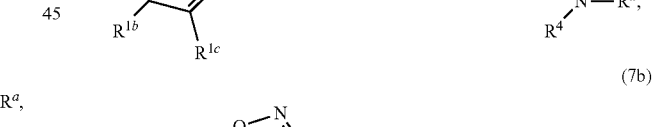

(7c)

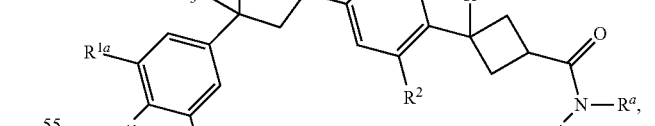

(7d)
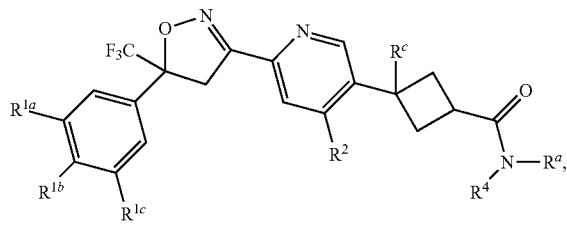
(7e)
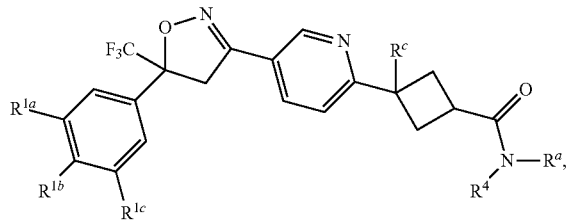
(7f)
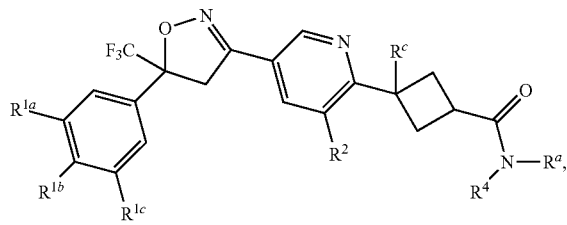
(8a)
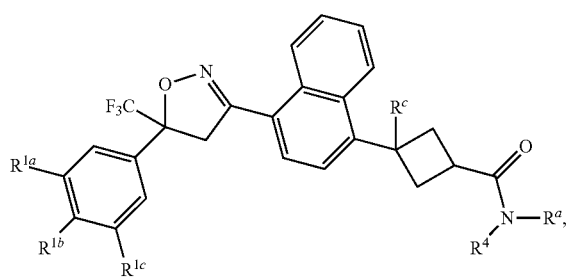
(9a)
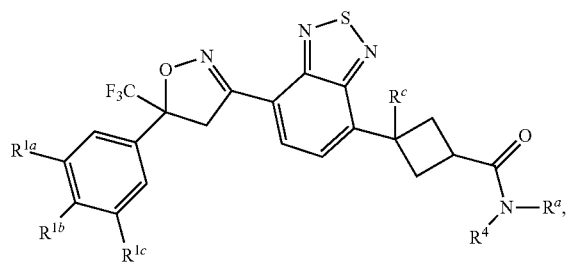
(10a)
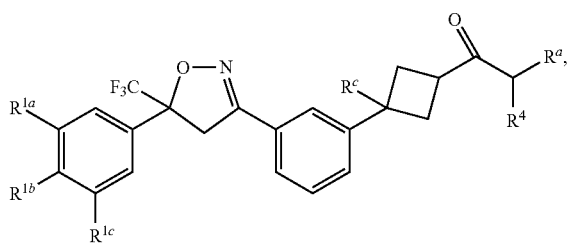
(11a)
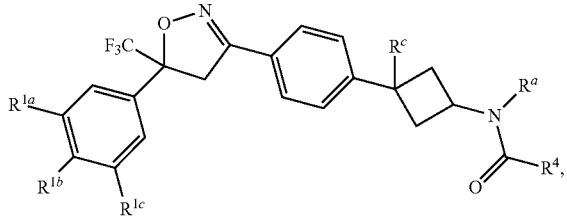
(11b)
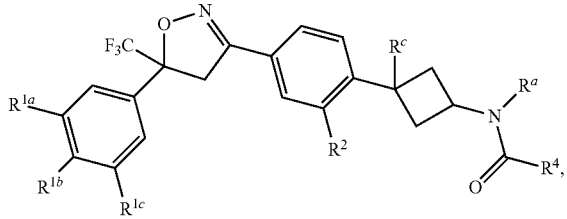
(11c)
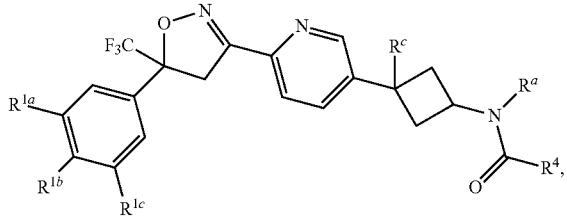
(11d)
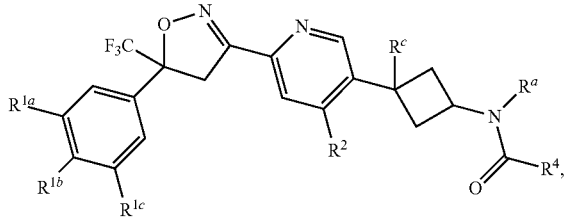
(11e)
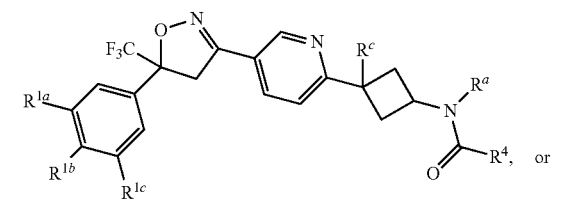
or
(11f)
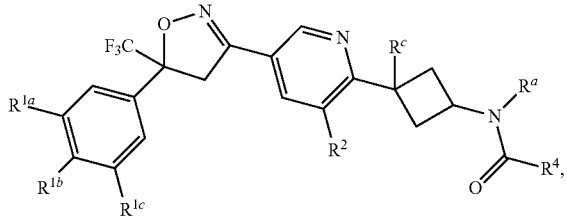
stereoisomers thereof, geometric isomers thereof, and veterinarily acceptable salts thereof.
In yet another aspect of the invention, are Formula (1) compounds having Formula (2a), (2b), (2c), (2d), (2e), (2f), (6a), (6b), (6c), (6d), (6e), (6f), (7a), (7b), (7c), (7d), (7e), (7f), (11a), (11b), (11c), (11d), (11e), (11f), and (11f), stereoisomers thereof, geometric isomers thereof, and veterinarily acceptable salts thereof.

In yet another aspect of the invention, are Formula (1) compounds having Formula (2a), (2b), (2c), (2d), (2e), and (2f), stereoisomers thereof, and veterinarily acceptable salts thereof. In yet another aspect of the invention, are Formula (1) compounds having Formula (6a), (6b), (6c), (6d), (6e), and (6f), stereoisomers thereof, and veterinarily acceptable salts thereof. In yet another aspect of the invention, are Formula (1) compounds having Formula (7a), (7b), (7c), (7d), (7e), and (7f), stereoisomers thereof, geometric isomers thereof, and veterinarily acceptable salts thereof. In yet another aspect of the invention, are Formula (1) compounds having Formula (11a), (11b), (11c), (11d), (11e), and (11f), stereoisomers thereof, geometric isomers thereof, and veterinarily acceptable salts thereof.

In yet another aspect of the invention, are Formula (1) compounds having Formula (2a), (2b), (6a) or (6b), stereoisomers thereof, and veterinarily acceptable salts thereof. In yet another aspect of the invention, are Formula (1) compounds having Formula (2a), stereoisomers thereof, and veterinarily acceptable salts thereof. In yet another aspect of the invention, are Formula (1) compounds having Formula (2b), stereoisomers thereof, and veterinarily acceptable salts thereof. In yet another aspect of the invention, are Formula (1) compounds having Formula (6a), stereoisomers thereof, and veterinarily acceptable salts thereof. In yet another aspect of the invention, are Formula (1) compounds having Formula (6b), stereoisomers thereof, and veterinarily acceptable salts thereof.

In yet another aspect of the invention, are Formula (1) compounds having Formula (2c), (2d), (6c), or (6d), stereoisomers thereof, and veterinarily acceptable salts thereof. In yet another aspect of the invention, are Formula (1) compounds having Formula (2c), stereoisomers thereof, and veterinarily acceptable salts thereof. In yet another aspect of the invention, are Formula (1) compounds having Formula (2d), stereoisomers thereof, and veterinarily acceptable salts thereof. In yet another aspect of the invention, are Formula (1) compounds having Formula (6c), stereoisomers thereof, and veterinarily acceptable salts thereof. In yet another aspect of the invention, are Formula (1) compounds having Formula (6d), stereoisomers thereof, and veterinarily acceptable salts thereof.

In yet another aspect of the invention, are Formula (1) compounds having Formula (2e), (2f), (6e), or (6f), stereoisomers thereof, and veterinarily acceptable salts thereof. In yet another aspect of the invention, are Formula (1) compounds having Formula (2e), stereoisomers thereof, and veterinarily acceptable salts thereof. In yet another aspect of the invention, are Formula (1) compounds having Formula (2f), stereoisomers thereof, and veterinarily acceptable salts thereof. In yet another aspect of the invention, are Formula (1) compounds having Formula (6e), stereoisomers thereof, and veterinarily acceptable salts thereof. In yet another aspect of the invention, are Formula (1) compounds having Formula (6f), stereoisomers thereof, and veterinarily acceptable salts thereof.

In yet another aspect of the invention, are Formula (1) compounds having Formula (3a), (4a), (4b), or (5a), stereoisomers thereof, and veterinarily acceptable salts thereof. In yet another aspect of the invention, are Formula (1) compounds having Formula (3a), stereoisomers thereof, and veterinarily acceptable salts thereof. In yet another aspect of the invention, are Formula (1) compounds having Formula (4a), stereoisomers thereof, and veterinarily acceptable salts thereof. In yet another aspect of the invention, are Formula (1) compounds having Formula (4b), stereoisomers thereof, and veterinarily acceptable salts thereof. In yet another aspect of the invention, are Formula (1) compounds having Formula (5a), stereoisomers thereof, and veterinarily acceptable salts thereof.

In yet another aspect of the invention, are Formula (1) compounds having Formula (7a), (7b), (11a), or (11b), stereoisomers thereof, geometric isomers thereof, and veterinarily acceptable salts thereof. In yet another aspect of the invention, are Formula (1) compounds having Formula (7a), stereoisomers thereof, geometric isomers thereof, and veterinarily acceptable salts thereof. In yet another aspect of the invention, are Formula (1) compounds having Formula (7b), stereoisomers thereof, geometric isomers thereof, and veterinarily acceptable salts thereof. In yet another aspect of the invention, are Formula (1) compounds having Formula (11a), stereoisomers thereof, geometric isomers thereof, and veterinarily acceptable salts thereof. In yet another aspect of the invention, are Formula (1) compounds having Formula (11b), stereoisomers thereof, geometric isomers thereof, and veterinarily acceptable salts thereof.

In yet another aspect of the invention, are Formula (1) compounds having Formula (7c), (7d), (11c), or (11d), stereoisomers thereof, geometric isomers thereof, and veterinarily acceptable salts thereof. In yet another aspect of the invention, are Formula (1) compounds having Formula (7c), geometric isomers thereof, stereoisomers thereof, and veterinarily acceptable salts thereof. In yet another aspect of the invention, are Formula (1) compounds having Formula (7d), stereoisomers thereof, and geometric isomers thereof, veterinarily acceptable salts thereof. In yet another aspect of the invention, are Formula (1) compounds having Formula (11c), stereoisomers thereof, geometric isomers thereof, and veterinarily acceptable salts thereof. In yet another aspect of the invention, are Formula (1) compounds having Formula (11d), stereoisomers thereof, geometric isomers thereof, and veterinarily acceptable salts thereof.

In yet another aspect of the invention, are Formula (1) compounds having Formula (7e), (7f), (11e), or (11f), stereoisomers thereof, geometric isomers thereof, and veterinarily acceptable salts thereof. In yet another aspect of the invention, are Formula (1) compounds having Formula (7e), stereoisomers thereof, geometric isomers thereof, and veterinarily acceptable salts thereof. In yet another aspect of the invention, are Formula (1) compounds having Formula (7f), stereoisomers thereof, geometric isomers thereof, and veterinarily acceptable salts thereof. In yet another aspect of the invention, are Formula (1) compounds having Formula (11e), stereoisomers thereof, geometric isomers thereof, and veterinarily acceptable salts thereof. In yet another aspect of the invention, are Formula (1) compounds having Formula (11f), stereoisomers thereof, geometric isomers thereof, and veterinarily acceptable salts thereof.

In yet another aspect of the invention, are Formula (1) compounds having Formula (8a), (9a), or (10a), stereoisomers thereof, and veterinarily acceptable salts thereof. In yet another aspect of the invention, are Formula (1) compounds having Formula (8a), stereoisomers thereof, and veterinarily acceptable salts thereof. In yet another aspect of the invention, are Formula (1) compounds having Formula (9a), stereoisomers thereof, and veterinarily acceptable salts thereof. In yet another aspect of the invention, are Formula (1) compounds having Formula (10a), stereoisomers thereof, and veterinarily acceptable salts thereof.

In yet another aspect of the invention when W is N then X is S. In yet another aspect of the invention, when W is $CR^c$, then X is S. In yet another aspect of the invention, when W is N, then X is $NR^6$. In yet another aspect of the invention, when W is $CR^c$, then X is S.

In another aspect of the invention, each of $R^{1a}$, $R^{1b}$, and $R^{1c}$ are independently selected from hydrogen, halo, cyano, $C_1$-$C_6$alkyl, $C_1$-$C_6$ haloalkyl, $C_0$-$C_3$alkyl$C_3$-$C_6$ cycloalkyl, and —$SF_5$. In yet another aspect of the invention, each of $R^{1a}$, $R^{1b}$, and $R^{1c}$ are independently selected from hydrogen, halo, cyano, $C_1$-$C_6$ haloalkyl, and $C_0$-$C_3$alkyl$C_3$-$C_6$cycloalkyl. In yet another aspect of the invention, each of $R^{1a}$, $R^{1b}$, and $R^{1c}$ are independently selected from hydrogen, halo, cyano, and $C_1$-$C_6$ haloalkyl. In yet another aspect of the invention, each of $R^{1a}$, $R^{1b}$, and $R^{1c}$ are independently selected from hydrogen, fluoro, chloro, cyano, and $C_1$-$C_6$ haloalkyl. In yet another aspect of the invention, each of $R^{1a}$, $R^{1b}$, and $R^{1c}$ are independently selected from hydrogen, fluoro, chloro, and $C_1$-$C_6$ haloalkyl. In yet another aspect of the invention, each of $R^{1a}$, $R^{1b}$, and $R^{1c}$ are independently selected from hydrogen, fluoro, chloro, and —$CF_3$.

In another aspect of the invention, the integer n of $(R^2)_n$ is 0. In yet another aspect of the invention, the integer n of $(R^2)_n$ is 2. When the integer n is 2, then each $R^2$ is independently halo, cyano, $C_1$-$C_6$alkyl, or hydroxyl. Further, when the integer n is 2, then each $R^2$ is independently halo, cyano, or hydroxyl. Further, when the integer n is 2, then each $R^2$ is independently bromo, chloro, fluoro, or cyano. In another aspect of the invention, the integer n of $(R^2)_n$ is 1. When the integer n is 1, then $R^2$ is halo, cyano, $C_1$-$C_6$alkyl, hydroxyl, or —OR. Further, when the integer n is 1, then $R^2$ is halo, cyano, $C_1$-$C_6$alkyl, or hydroxyl. Further, when the integer n is 1, then $R^2$ is halo, cyano, methyl, or hydroxyl. Further, when the integer n is 1, then $R^2$ is bromo, chloro, fluoro, cyano, methyl, or hydroxyl. Further, when the integer n is 1, then $R^2$ is bromo, chloro, fluoro, or cyano. In yet another aspect of the invention when the integer n is 1, then $R^2$ is bromo, chloro, or fluoro.

In another aspect of the invention, $R^3$ is —C(O)$NR^aR^4$ or —$NR^aC(O)R^4$. In another aspect of the invention, $R^3$ is —C(O)$NR^aR^4$.

In another aspect of the invention, when $R^3$ is —C(O)$NR^aR^4$, then $R^a$ is hydrogen, $C_1$-$C_6$alkyl, $C_0$-$C_3$alkyl$C_3$-$C_6$cycloalkyl, C(O)$R^4$, or C(O)OR. In yet another aspect of the invention, $R^a$ is hydrogen, $C_1$-$C_6$alkyl, $C_0$-$C_3$alkyl$C_3$-$C_6$cycloalkyl, or C(O)$R^4$. In yet another aspect of the invention, $R^a$ is hydrogen, $C_1$-$C_6$alkyl, or $C_0$-$C_3$alkyl$C_3$-$C_6$cycloalkyl. In yet another aspect of the invention, $R^a$ is hydrogen, methyl, ethyl, cyclopropyl, or cyclobutyl. The $R^a$ alkyl and alkylcycloalkyl moieties can be optionally substituted as described herein. In another aspect of the invention, when $R^3$ is —C(O)$NR^aR^4$, then $R^4$ is hydrogen, $C_1$-$C_6$alkyl, $C_0$-$C_3$alkyl$C_3$-$C_6$cycloalkyl, $C_0$-$C_3$alkylphenyl, or $C_0$-$C_3$alkylheteroaryl. In yet another aspect of the invention, $R^4$ is hydrogen, $C_1$-$C_6$alkyl, $C_0$-$C_3$alkyl$C_3$-$C_6$cycloalkyl, or $C_0$-$C_3$alkylphenyl. In yet another aspect of the invention, $R^4$ is hydrogen, $C_1$-$C_6$alkyl, or $C_0$-$C_3$alkyl$C_3$-$C_6$cycloalkyl. In yet another aspect of the invention, $R^4$ is $C_1$-$C_6$alkyl or $C_0$-$C_3$alkyl$C_3$-$C_6$cycloalkyl. Each of $R^4$ phenyl, heteroaryl, and heterocycle moieties can be optionally substituted, when chemically possible, with one or more substituents as described herein. Further, each of $R^4$ alkyl or alkylcycloalkyl moieties can be optionally substituted, when chemically possible, as described herein.

In another aspect of the invention, $R^5$ is cyano, $C_1$-$C_6$alkyl, or $C_1$-$C_6$haloalkyl. In yet another aspect of the invention, $R^5$ is cyano, methyl, ethyl, or trifluoromethyl. In yet another aspect of the invention, $R^5$ is cyano, methyl, or trifluoromethyl. In yet another aspect of the invention, $R^5$ is cyano or trifluoromethyl. In yet another aspect of the invention, $R^5$ is trifluoromethyl.

In yet another aspect of the invention, $R^6$ is cyano, $C_1$-$C_6$alkyl, $C_1$-$C_6$haloalkyl, or —C(O)$NH_2$. In yet another aspect of the invention, $R^6$ is cyano, $C_1$-$C_6$alkyl, or $C_1$-$C_6$haloalkyl. In yet another aspect of the invention, $R^6$ is cyano, methyl, ethyl, or $C_1$-$C_6$haloalkyl. In yet another aspect of the invention, $R^6$ is cyano, methyl, or $C_1$-$C_6$haloalkyl. In yet another aspect of the invention, $R^6$ is cyano or $C_1$-$C_6$haloalkyl. In yet another aspect of the invention, $R^6$ is $C_1$-$C_6$haloalkyl. In yet another aspect of the invention, $R^6$ is —$CF_3$, —$CHF_2$, —$CH_2F$, and —$CF_2Cl$. In yet another aspect of the invention, $R^6$ is —$CF_3$, —$CHF_2$, and —$CH_2F$. In yet another aspect of the invention, $R^6$ is —$CF_3$.

In yet another aspect of the invention are compounds of Formula (1) selected from:

3-hydroxy-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;

3-hydroxy-3-{4-[5-(3,4,5-trichloro-phenyl)-5-trifluoromethyl-4,5-dihydro-isoxazol-3-yl]-phenyl}-cyclobutanecarboxylic acid cyclopropylamide;

3-hydroxy-3-{4-[5-(3,4,5-trichloro-phenyl)-5-trifluoromethyl-4,5-dihydro-isoxazol-3-yl]-phenyl}-cyclobutanecarboxylic acid methylamide;

3-hydroxy-3-{4-[5-(3,4,5-trichloro-phenyl)-5-trifluoromethyl-4,5-dihydro-isoxazol-3-yl]-phenyl}-cyclobutanecarboxylic acid dimethylamide;

3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide;

3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide;

3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;

3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;

3-fluoro-3-{4-[5-(3,4,5-trichloro-phenyl)-5-trifluoromethyl-4,5-dihydro-isoxazol-3-yl]-phenyl}-cyclobutanecarboxylic acid methylamide;

3-fluoro-3-{4-[5-(3,4,5-trichloro-phenyl)-5-trifluoromethyl-4,5-dihydro-isoxazol-3-yl]-phenyl}-cyclobutanecarboxylic acid methylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid;
3-fluoro-3-{4-[5-(3,4,5-trichloro-phenyl)-5-trifluoromethyl-4,5-dihydro-isoxazol-3-yl]-phenyl}-cyclobutanecarboxylic acid ethylamide;
3-fluoro-N-(2-oxo-2-((2,2,2-trifluoroethyl)amino)ethyl)-3-(4-(5-(3,4,5-trichlorophenyl)-5-(trifluoromethyl)-4,5-dihydroisoxazol-3-yl)phenyl)cyclobutanecarboxamide;
1-{4-[5-(3,4,5-trichloro-phenyl)-5-trifluoromethyl-4,5-dihydro-isoxazol-3-yl]-phenyl}-azetidine-3-carboxylic acid cyclopropylamide;
1-{4-[5-(3,4,5-trichloro-phenyl)-5-trifluoromethyl-4,5-dihydro-isoxazol-3-yl]-phenyl}-azetidine-3-carboxylic acid methylamide;
1-{4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide;
1-{4-[5-(3,4,5-trichloro-phenyl)-5-trifluoromethyl-4,5-dihydro-isoxazol-3-yl]-phenyl}azetidine-3-carboxylic acid dimethylamide;
1-{2-chloro-4-[5-(3,4,5-trichloro-phenyl)-5-trifluoromethyl-4,5-dihydro-isoxazol-3-yl]-phenyl}-azetidine-3-carboxylic acid methylamide;
1-{2-chloro-4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide;
1-{2-chloro-4-[5-(3,4,5-trichloro-phenyl)-5-trifluoromethyl-4,5-dihydro-isoxazol-3-yl]-phenyl}-azetidine-3-carboxylic acid cyclopropylamide;
1-{2-chloro-4-[5-(3,4,5-trichloro-phenyl)-5-trifluoromethyl-4,5-dihydro-isoxazol-3-yl]-phenyl}-azetidine-3-carboxylic acid dimethylamide;
N-(3-fluoro-3-(4-(5-(3,4,5-trichlorophenyl)-5-(trifluoromethyl)-4,5-dihydroisoxazol-3-yl)phenyl)cyclobutyl)cyclopropanecarboxamide; and
N-(3-fluoro-3-(4-(5-(3,4,5-trichlorophenyl)-5-(trifluoromethyl)-4,5-dihydroisoxazol-3-yl)phenyl)cyclobutyl)-2-(methylsulfonyl)acetamide, stereoisomers thereof, geometric isomers thereof, and veterinarily acceptable salts thereof.

In yet another aspect of the invention are compounds of Formula (1) selected from:
3-hydroxy-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;
3-hydroxy-3-{4-[5-(3,4,5-trichloro-phenyl)-5-trifluoromethyl-4,5-dihydro-isoxazol-3-yl]-phenyl}-cyclobutanecarboxylic acid cyclopropylamide;
3-hydroxy-3-{4-[5-(3,4,5-trichloro-phenyl)-5-trifluoromethyl-4,5-dihydro-isoxazol-3-yl]-phenyl}-cyclobutanecarboxylic acid methylamide;
3-hydroxy-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;
3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;
3-fluoro-3-{4-[5-(3,4,5-trichloro-phenyl)-5-trifluoromethyl-4,5-dihydro-isoxazol-3-yl]-phenyl}-cyclobutanecarboxylic acid methylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid methylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid;
3-fluoro-3-{4-[5-(3,4,5-trichloro-phenyl)-5-trifluoromethyl-4,5-dihydro-isoxazol-3-yl]-phenyl}-cyclobutanecarboxylic acid ethylamide;
3-fluoro-N-(2-oxo-2-((2,2,2-trifluoroethyl)amino)ethyl)-3-(4-(5-(3,4,5-trichlorophenyl)-5-(trifluoromethyl)-4,5-dihydroisoxazol-3-yl)phenyl)cyclobutanecarboxamide;
N-(3-fluoro-3-(4-(5-(3,4,5-trichlorophenyl)-5-(trifluoromethyl)-4,5-dihydroisoxazol-3-yl)phenyl)cyclobutyl)cyclopropanecarboxamide; and
N-(3-fluoro-3-(4-(5-(3,4,5-trichlorophenyl)-5-(trifluoromethyl)-4,5-dihydroisoxazol-3-yl)phenyl)cyclobutyl)-2-(methylsulfonyl)acetamide, stereoisomers thereof, geometric isomers thereof, and veterinarily acceptable salts thereof.

In yet another aspect of the invention are compounds of Formula (1) selected from:
1-{4-[5-(3,4,5-trichloro-phenyl)-5-trifluoromethyl-4,5-dihydro-isoxazol-3-yl]-phenyl}-azetidine-3-carboxylic acid cyclopropylamide;
1-{4-[5-(3,4,5-trichloro-phenyl)-5-trifluoromethyl-4,5-dihydro-isoxazol-3-yl]-phenyl}-azetidine-3-carboxylic acid methylamide;
1-{4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide;
1-{4-[5-(3,4,5-trichloro-phenyl)-5-trifluoromethyl-4,5-dihydro-isoxazol-3-yl]-phenyl}azetidine-3-carboxylic acid dimethylamide;
1-{2-chloro-4-[5-(3,4,5-trichloro-phenyl)-5-trifluoromethyl-4,5-dihydro-isoxazol-3-yl]-phenyl}-azetidine-3-carboxylic acid methylamide;
1-{2-chloro-4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide;
1-{2-chloro-4-[5-(3,4,5-trichloro-phenyl)-5-trifluoromethyl-4,5-dihydro-isoxazol-3-yl]-phenyl}-azetidine-3-carboxylic acid cyclopropylamide; and
1-{2-chloro-4-[5-(3,4,5-trichloro-phenyl)-5-trifluoromethyl-4,5-dihydro-isoxazol-3-yl]-phenyl}-azetidine-3-carboxylic acid dimethylamide, stereoisomers thereof, geometric isomers thereof, and veterinarily acceptable salts thereof.

In another aspect of the invention, is a veterinary composition that comprises a) a Formula (1) compounds, stereoisomers thereof, stereoisomers thereof, geometric isomers thereof, and veterinarily acceptable salts thereof, and (b) a veterinarily acceptable excipient, diluent, or carrier. Preferably, the composition comprises a therapeutically effective amount of a Formula (1) compounds, stereoisomer thereof, geometric isomers thereof, and veterinarily acceptable salts thereof, and a veterinarily acceptable excipient, diluent, or carrier.

The composition may comprise at least one additional veterinary agent. Preferred additional veterinary agents include endoparasiticides, endectocides, ectoparasiticides, insecticides, and anthelmintics, and are described herein.

The composition may comprise at least one additional veterinary agent. Preferred additional veterinary agents include endoparasiticides, endectocides, ectoparasiticides, insecticides, and anthelmintics, and are described herein. In one aspect of the invention, the additional veterinary agent is selected from amitraz, amino acetonitriles, anthelmintics (e.g., albendazole, cambendazole, fenbendazole, flubendazole, mebendazole, octadepsipeptides, oxfendazole, oxibendazole, paraherquamide, parbendazole, piperazines, praziquantel, thiabendazole, tetramisole, triclabendazole, levamisole, pyrantel pamoate, oxantel, morantel, and the like), avermectins (e.g., abamectin, doramectin, emamectin, eprinomectin, ivermectin, moxidectin, selamectin, and the like), milbemycin, milbemycin oxime, demiditraz, diethylcarbamazine, fipronil, hydroprene, kinoprene, methoprene, metaflumizone, niclosamide, permethrin, pyrethrins, pyriproxyfen, and spinosad. In another aspect of the invention, the additional agent is selected from an amino acetonitrile, albendazole, cambendazole, fenbendazole, flubendazole, mebendazole, oxfendazole, oxibendazole, paraherquamide, parbendazole, praziquantel, thiabendazole, tetramisole, triclabendazole, levamisole, pyrantel pamoate, oxantel, morantel, abamectin, doramectin, emamectin, eprinomectin, ivermectin, moxidectin, selamectin, milbemycin, milbemycin oxime, demiditraz, diethylcarbamazine, fipronil, hydroprene, kinoprene, methoprene, metaflumizone, niclosamide, pyriproxyfen, and spinosad. In yet another aspect of the invention, the additional agent is selected from an amino acetonitrile, paraherquamide, praziquantel, abamectin, doramectin, emamectin, eprinomectin, ivermectin, moxidectin, selamectin, milbemycin, and milbemycin oxime. In yet another aspect of the invention, the additional agent is selected from abamectin, doramectin, emamectin, eprinomectin, ivermectin, moxidectin, selamectin, milbemycin, and milbemycin oxime. In yet another aspect of the invention, the additional agent is selected from abamectin, doramectin, eprinomectin, ivermectin, moxidectin, selamectin, milbemycin, and milbemycin oxime. In yet another aspect of the invention, the additional agent is selected from moxidectin, selamectin, and milbemycin oxime. In yet another aspect of the invention, the additional agent is selected from moxidectin and milbemycin oxime.

In yet another aspect of the invention is the use of a Formula (1) compound for the manufacture of a medicament.

In yet another aspect of the invention is a method for treating a parasitic infection or infestation in an animal that includes the step of administering to said animal, in need of such treatment, a therapeutically effective amount of a compound of the present invention, stereoisomer thereof, geometric isomer thereof, or veterinarily acceptable salt thereof. In one aspect, the animal is a mammal, specifically a companion animal (for example, dog, cat, or horse) or livestock (for example, sheep, goat, cattle, and pig). In another aspect, the animal is a bird, specifically, fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferably, the compounds of the present invention, and compositions thereof, can be administered to the animal orally or topically.

In yet another aspect of the invention is a method for treating a parasitic infection or infestation in an animal that includes the step of administering to said animal, in need of such treatment, a therapeutically effective amount of a compound of the present invention, stereoisomer thereof, geometric isomer thereof, or veterinarily acceptable salt thereof, in combination with at least one additional veterinary agent. In one aspect, the animal is a mammal, specifically a companion animal (for example, dog, cat, or horse) or livestock (for example, sheep, goat, cattle, and pig). In another aspect, the animal is a bird, specifically, fowl (for example, chicken, turkey, duck, and geese). In another aspect, the animal is a fish. The compounds of the present invention, and compositions thereof, can be administered to the animal orally or topically. The compounds of the present invention, and compositions thereof, can also be administered to the animal by intramuscular-, intraperitoneal-, or subcutaneous-injection. Preferably, the compounds of the present invention, and compositions thereof, can be administered to the animal orally or topically. Equally preferred, the compounds of the present invention can be administered by injection.

Compounds of the present invention alone, or in combination with an additional veterinary agent(s) may be administered as (a) a single veterinary composition which comprises a compound of the present invention, stereoisomer thereof, geometric isomer thereof, veterinarily acceptable salt thereof, and optionally, at least one additional veterinary agent as described herein and a veterinarily acceptable excipient, diluent, or carrier; or (b) two separate veterinary compositions comprising (i) a first composition comprising a compound of the present invention, stereoisomer thereof, geometric isomer thereof, veterinarily acceptable salt thereof, and a veterinarily acceptable excipient, diluent, or carrier, and (ii) a second composition comprising at least one additional veterinary agent, as described herein and a veterinarily acceptable excipient, diluent, or carrier. The veterinary compositions may be administered simultaneously or sequentially and in any order.

All of the recited WO patent publications herein are incorporated by reference.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —$OCH_3$, —$OCH_2CH_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "$(C_1-C_6)$alkyl" refers to a monovalent, straight or branched aliphatic group containing 1 to 6 carbon atoms. Non-exclusive examples of $(C_1-C_6)$alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The alkyl moiety may be attached to the chemical moiety by any one of the carbon atoms of the aliphatic chain. Alkyl groups are optionally substituted as described herein. Further when used in compound words such as alkylphenyl, said alkyl moiety has the same meaning as herein defined and may be attached to the chemical moiety by any one of the carbon atoms of the aliphatic chain. Non-limiting examples of the compound word, alkylphenyl include: $C_1$alkylphenyl is —$CH_2$-phenyl, $C_2$alkylphenyl is —$CH_2CH_2$phenyl, $C_0$alkylphenyl is phenyl, and the like.

"Alkenyl" as used herein, unless otherwise indicated, refers to a straight or branched aliphatic hydrocarbon chain having 2- to 6-carbon atoms and containing at least one carbon-carbon double bond (for example —C=C—, or —C=$CH_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Alkynyl" as used herein, unless otherwise indicated, refers to straight or branched aliphatic hydrocarbon chain having 2- to 6-carbon atoms and containing at least one carbon-carbon triple bond (for example, —C≡C— or —C≡CH). Non-exclusive examples of alkynyl include: ethynyl, 2-propynyl, 1-methyl-2-propynyl, 2-butynyl, 3-butynyl, 2-methyl-3-butynyl, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Chiral", as used herein, refers to the structural characteristic of a molecule that makes it impossible to superimpose it on its mirror image, (e.g., "R" and "S" enantiomers). In some instances, chirality is depicted by a "*" within the formula.

"Compounds of the present invention", as used herein, unless otherwise indicated, refers to compounds of Formula (1), stereoisomers thereof. Further, some compounds of the present invention can exist as geometric isomers, e.g., cis and trans isomers, which are also represented by the single bond "∿" in the Schemes, Preparations, and Examples.

"Cycloalkyl", as used herein, unless otherwise indicated, includes fully saturated or partially saturated carbocyclic alkyl moieties. Non-limiting examples of partially saturated cycloalkyls include: cyclopropene, cyclobutene, cycloheptene, cyclooctene, cyclohepta-1,3-diene, and the like. Preferred cycloalkyls are 3- to 6-membered saturated monocyclic rings including cyclopropyl, cyclobutyl, cyclopentyl, and cyclohexyl. The cycloalkyl group may be attached to the chemical moiety by any one of the carbon atoms within the carbocyclic ring. Cycloalkyl groups are optionally substituted with at least one substituent. Further when used in compound words such as alkylcycloalkyl, said alkyl and cycloalkyl moiety has the same meaning as herein defined and may be attached to the chemical moiety by any one of the carbon atoms of the aliphatic chain. Examples of $C_0$-$C_6$alkyl$C_3$-$C_6$cycloalkyl include, methylcyclopropane ($C_1$alkyl$C_3$cycloalkyl or —$CH_2$cyclopropane), ethylcyclopropane ($C_2$alkyl$C_3$cycloalkyl or —$CH_2CH_2$cyclopropane), methylcyclobutane ($C_1$alkyl$C_4$cycloalkyl or —$CH_2$cyclobutane), ethylcyclobutane ($C_2$alkyl$C_4$cycloalkyl or —$CH_2CH_2$cyclobutane), methylcyclohexane ($C_1$alkyl$C_6$cycloalkyl or —$CH_2$cyclohexane), and the like. $C_0$alkyl$C_3$-$C_6$cycloalkyl is $C_3$-$C_6$cycloalkyl. Cycloalkyl moieties are optionally substituted as described herein "Halogen" or "halo", as used herein, unless otherwise indicated, refers to fluorine, chlorine, bromine and iodine. Further, when used in compound words such as "haloalkyl", "haloalkoxy", "haloalkenyl", or "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C$—, $ClCH_2$—, $CF_3CH_2$— and $CF_3CCl_2$—, and the like. The term "haloalkoxy" is defined analogously to the term "haloalkyl". Examples of "haloalkoxy" include $CF_3O$—, $CCl_3CH_2O$—, $HCF_2CH_2CH_2O$— and $CF_3CH_2O$—, and the like. The term "haloalkenyl is defined analogously to the term "haloalkyl" except that the aliphatic chain contains at least one carbon-carbon double bond. Examples of "haloalkenyl" include $CF_3C$=C—, $CCl_3C$=C—, $HCF_2C$=C— and $CF_3C$=CC—, and the like. The term "haloalkynyl" is defined analogously to the term "haloalkyl" except that the aliphatic chain contains at least one carbon-carbon triple bond. Examples of "haloalkynyl" include $CF_3C$≡C—, $CCl_3C$≡C—, $HCF_2C$≡C— and $CF_3C$≡CC—, and the like.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, or S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The heteroaryl group may be attached to the chemical moiety by any one of the carbon atoms or nitrogen heteroatoms within the monocyclic or fused ring. Further when used in compound words such as alkylheteroaryl, said alkyl and heteroaryl moiety have the same meaning as herein defined and may be attached to the chemical moiety by any one of the carbon atoms of the aliphatic chain. For example, $C_0$alkylheteroaryl is heteroaryl, $C_1$alkylheteroaryl is —$CH_2$heteroaryl, $C_0$alkylheteroaryl is —$CH_2CH_2$heteroaryl, and the like. Heteroaryls are optionally substituted as described herein.

"Heterocycle", as used herein, unless otherwise indicated, refers to a partially saturated or saturated 3- to 6-membered monocyclic ring containing one or more heteroatoms each independently selected from N, O, or S, preferably from one to four heteroatoms. Non-exclusive examples of heterocycle include oxiranyl, aziridinyl, oxetanyl, azetidinyl, tetrahydrofuran, tetrahydrothiophene, pyrrolidinyl, tetrahydropyranyl, piperidinyl, piperazinyl, tetrahydropyridinyl, 2H-azirine, 2,3-dihydro-azete, 3,4-dihydro-2H-pyrrole, and the like. The heterocycle group may be attached to the chemical moiety by any one of the carbon atoms or nitrogen heteroatoms within the monocyclic ring. Further when used in compound words such as alkylheterocycle, said alkyl and heterocycle moiety have the same meaning as herein defined and may be attached to the chemical moiety by any one of the carbon atoms of the aliphatic chain. For example, $C_0$alkylheterocycle is heterocycle, $C_1$alkylheterocycle is —$CH_2$heterocycle, $C_0$alkylheterocycle is —$CH_2CH_2$heterocycle, and the like. Heterocycles are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like), bed bugs, and lice. Preferred compounds of the present invention can be used for the treatment of parasites, i.e., treatment of a parasitic infection or infestation.

"Therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the mammal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to a mammal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the mammal being treated therewith. The term "pharmaceutically" acceptable has the same meaning as that recited for "veterinarily" acceptable.

DETAILED DESCRIPTION

The present invention provides Formula (1) compounds, stereoisomers thereof, geometric isomers thereof, as well as veterinary compositions that are useful as antiparasitic agents for animals and birds, in particular, compounds that act as ectoparasiticides.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie*, 4, Aufl. ed. Springer-Verlag, Berlin, including supplements (also available via the Beilstein online database)).

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organischen Chemie*, 4, Aufl. ed. Springer-Verlag, Berlin, including supplements (also available via the Beilstein online database)). For illustrative purposes, the reaction schemes depicted below demonstrate potential routes for synthesizing compounds of the present invention, and key intermediates. For a more detailed description of the individual reaction steps, see the Examples section below. A skilled artisan will appreciate that other suitable starting materials, reagents, and synthetic routes may be used to synthesize the compounds of the present invention and a variety of derivatives thereof. Further, many of the compounds prepared by the methods described below can be further modified in light of this disclosure using conventional chemistry well known to the skilled artisan.

Compounds of the present invention described herein contain at least one asymmetric or chiral center; and, therefore, exist in different stereoisomeric forms. The R and S configurations are based upon knowledge of known chiral inversion/retention chemistry. Unless specified otherwise, it is intended that all stereoisomeric forms of the compounds of the present invention as well as mixtures thereof, including racemic mixtures and diastereomeric mixtures, form part of the present invention.

Enantiomeric mixtures can be separated into their individual enantiomers on the basis of their physical chemical differences by methods well known to those skilled in the art, such as chromatography and/or fractional crystallization. A more detailed description of techniques that can be used to resolve stereoisomers of compounds from their racemic mixture can be found in Jean Jacques Andre Collet, Samuel H. Wilen, Enantiomers, Racemates and Resolutions, John Wiley and Sons, Inc. (1981).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula 1 are depicted as Formula 1a and Formula 1b involving the spirocyclic isoxazoline chiral center identified with an asterisk (*). Similarly, the preparations and Examples herein share the same chiral center. Molecular depictions drawn herein follow standard conventions for depicting stereochemistry.

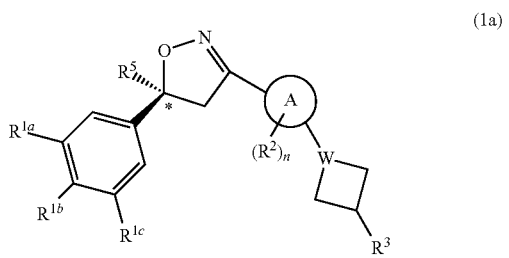

(1a)

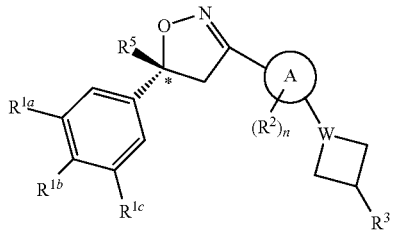

(1b)

For illustrative purposes, the reaction schemes depicted below demonstrate potential routes for synthesizing key intermediates and compounds of the present invention. Those skilled in the art will appreciate that other suitable starting materials, reagents, and synthetic routes may be used to synthesize the intermediates and compounds of the present invention and a variety of derivatives thereof. Schemes 1-6 outline the general procedures useful for the preparation of compounds of the present invention. It is to be understood, however, that the invention, as fully described herein and as recited in the claims, is not intended to be limited by the details of the following schemes or modes of preparation.

In the Schemes below, the following catalysts/reactants include: tetrahydrofuran (THF); bis(triphenylphosphine) palladium II chloride Pd(PPh$_3$)$_2$Cl$_2$ from Strem; bis(1,5-cyclooctadiene)di-mu-methoxyiiridum(I) (Ir[COD])$_2$) from Aldrich; 4,4,4',4',5,5,5',5'-octamethyl[2,2'-bi-1,3,2-dioxaborolane] (B$_2$pin$_2$) from Aldrich; and 4,4'-di-tert-butyl-2,2'-bypyridine (dtbpy) from Aldrich; triethylamine (Et$_3$N); diisopropylethyl amine (DIPEA); N,N,N',N'-Tetramethyl-O-(7-azabenzotriazol-1-yl)uronium hexafluorophosphate (HATU); 1-ethyl-3-(3-dimethylaminopropyl)carbodiimide (EDCl); 1-hydroxybenzotriazole hydrate (HOBt); methyl iodide (MeI); N,N-dimethyl formamide (DMF); N—N-dimethylsulfoxide (DMSO); N-chloro-succinimide (NCS); diphenylphosphoryl azide (DPPA); and isopropylamine (iPrNH$_2$).

Scheme 1

1A

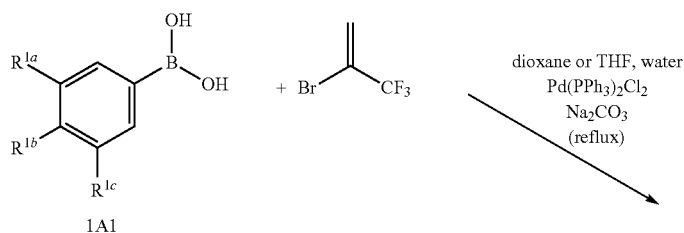

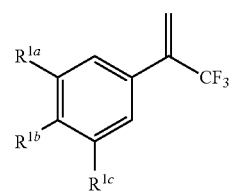

1B or

1C

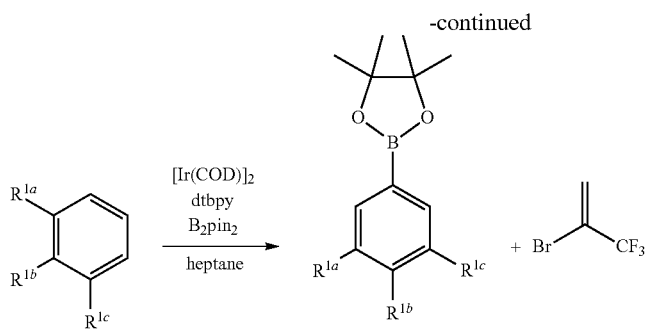
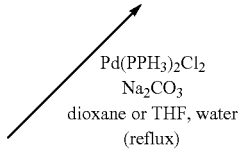

$R^{1a}$, $R^{1b}$, and $R^{1c}$ are as defined herein.

The aryl olefins (1C) can be prepared according to Scheme 1. The requisite organoborates can be prepared as boronate ester intermediates (1B2) from literature methods (*Org. Lett.* 2007, 9, 761-764) or purchased as boronic acids (1A1) such as 3,5-dichloroboronic acid from Aldrich. Intermediate 1A1 or 1B2 compounds can be added to dioxane or THF and water, followed by 2-bromo-3,3,3-trifluoropropene, potassium carbonate, and bis(triphenylphosphine) palladium II chloride to afford the aryl olefins (1C).

Scheme 2

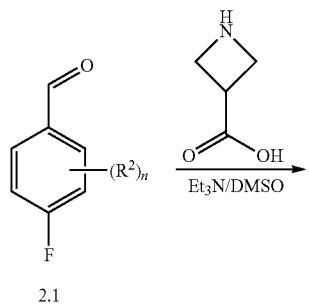

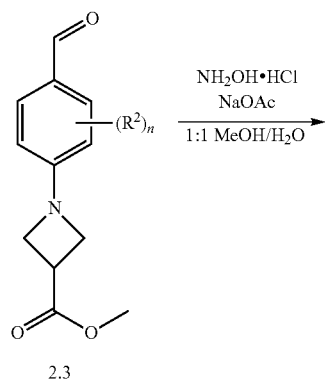

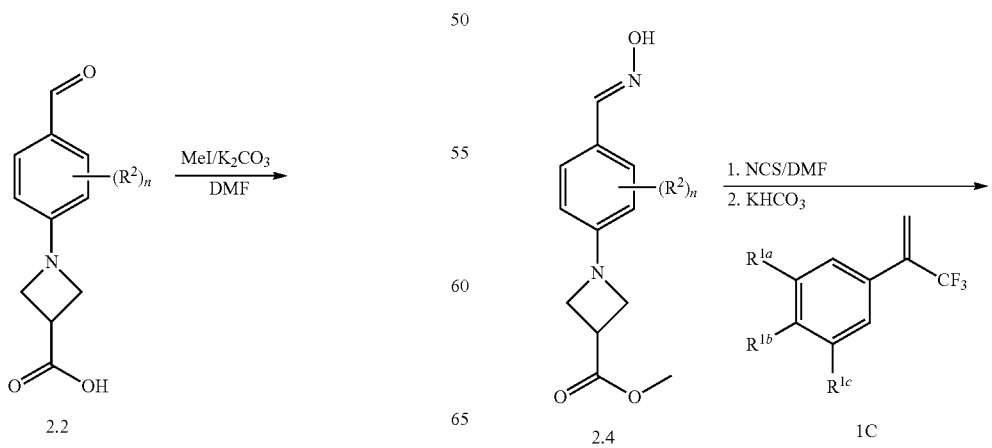

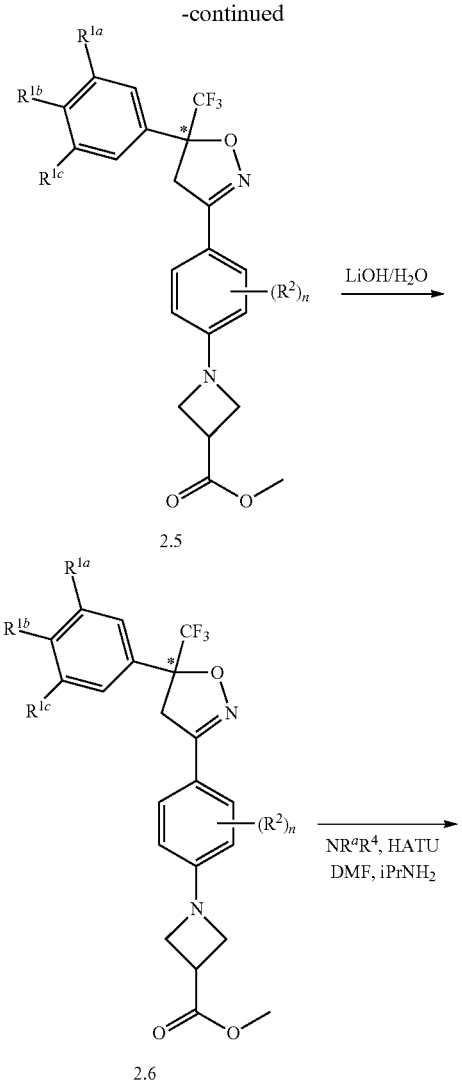

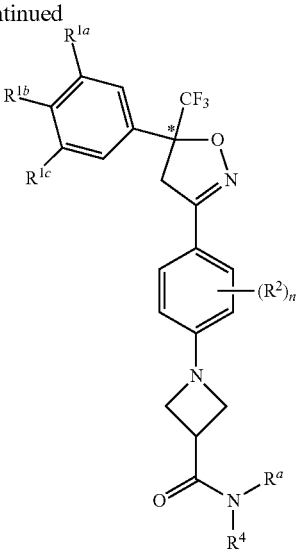

(2.7)

$R^{1a}$, $R^{1b}$, $R^{1c}$, $R^2$, $R^a$, $R^4$ and n are as defined herein. The "*" represents a chiral center, e.g., "S" or "R" enantiomers.

The phenyl azetidines can be prepared as shown in Scheme 2. Amination of commercially available aldehyde 2.1 followed by esterification of carboxylic acid 2.2 gave aldehyde intermediate 2.3. The aldehyde is condensed with hydroxylamine to provide the oxime 2.4. From the oxime, the isoxazoline ring can be prepared in a one-pot, two step process. Treatment of the oxime with N-chlorosuccinimide provides the chlorooxime which undergoes [3+2] cyclization with aryl olefins 1C to provide the isoxazoline ester 2.5. These steps can also be done as separate reactions. The isoxazoline ester 2.5 can be hydrolyzed to the acid 2.6 with aqueous lithium hydroxide. Amide (2.7) formation can be accomplished by coupling the acid 2.6 with an amine using a condensing agent such as HATU or HOBt. The amides (2.7) can be further converted to the corresponding thioamides by treatment with Lawesson's reagent or $P_2S_5$.

Scheme 3

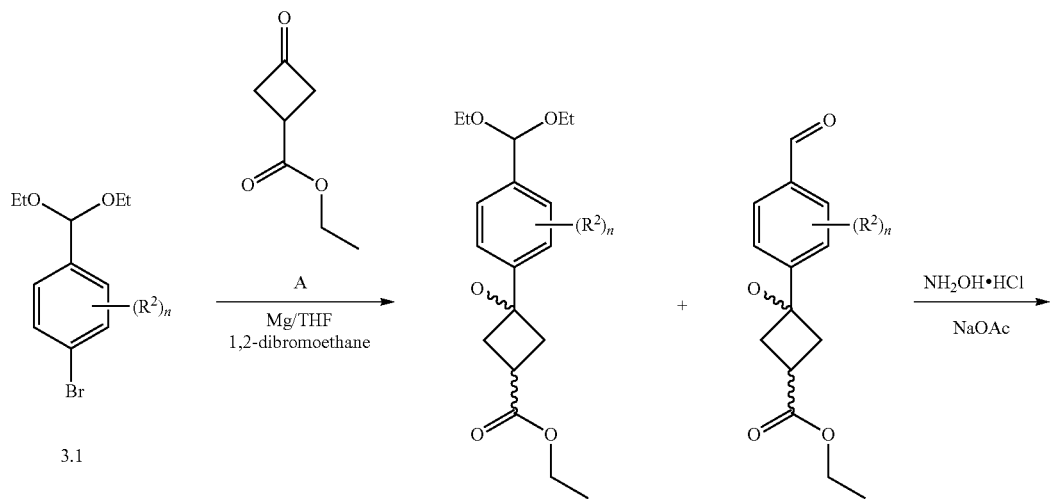

-continued
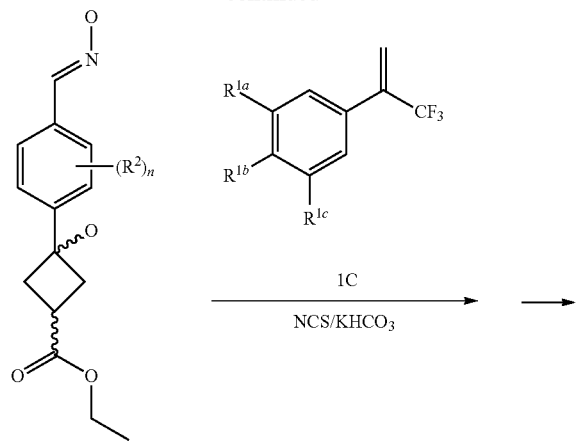
3.3 (a and b)
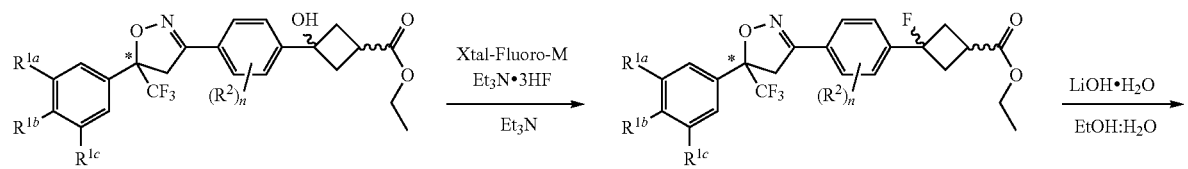
3.4 (a and b)          3.5 (a and b)
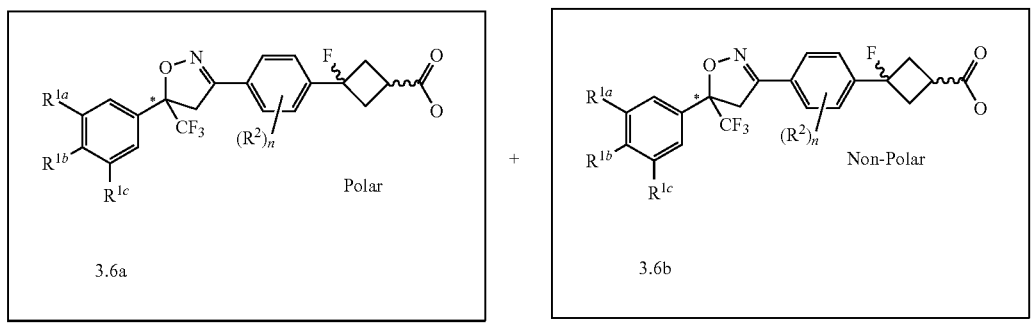
3.6a      3.6b
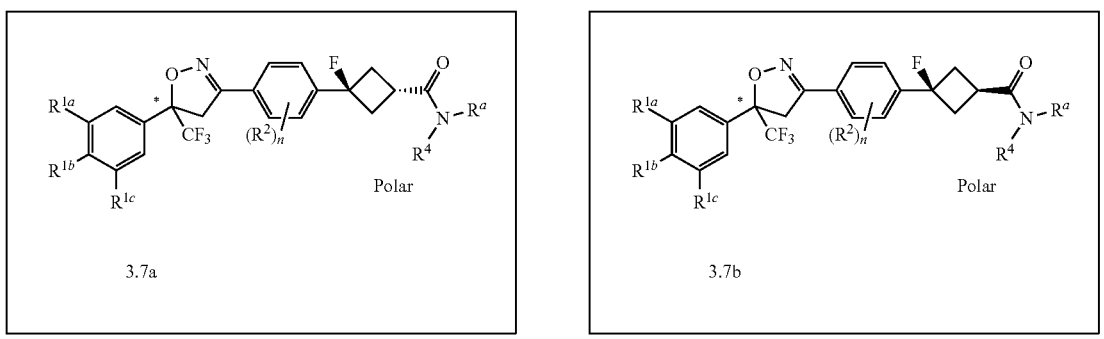
3.7a      3.7b
$R^{1a}$, $R^{1b}$, $R^{1c}$, $R^2$, $R^a$, $R^4$, and $n$ are as defined herein. The "*" represents a chiral center, e.g., "S" or "R" enantiomers, and the "〰" bond represents geometric isomerism, e.g., cis and trans isomers.

The phenyl cyclobutanes can be prepared as shown in Scheme 3. Reaction of 4-bromobenzaldehyde diethylacetal (3.1) with Mg metal or iPrMgCl provides an organometallic reagent that adds to ethyl 3-oxocyclobutane-carboxylate (A) to give a mixture of the diethylacetal (3.2.1) and the aldehyde (3.2.2) as mixtures of cis- and trans-isomers (a and b). Condensation with hydroxylamine provides the oximes as a mixture of isomers (3.3a and b). Chlorination and cyclization with aryl olefins (1C) as described in Scheme 2 provides the isoxazolines (3.4) (still a mixture of isomers in the cyclobutane ring). Fluorination of the hydroxyl group can be achieved by reaction with Xtaflor-E to provide the fluorocyclobutanes (3.5) as a mixture of cis- and trans-isomers (a and b). The ester (3.5) can be hydrolyzed to the acid (3.6) with aqueous lithium hydroxide. At this point, the cis and trans isomers are separated by chromatography and the acids (3.6a) and (3.6b) are taken on independently to amides. Amide (3.7a and 3.7b) formation can be accomplished by coupling the acid (3.6a and 3.6b) with an amine using a condensing agent such as HATU or HOBt. The amides (3.7a and 3.7b) can be further converted to the corresponding thioamides by treatment with Lawesson's reagent or $P_2S_5$.

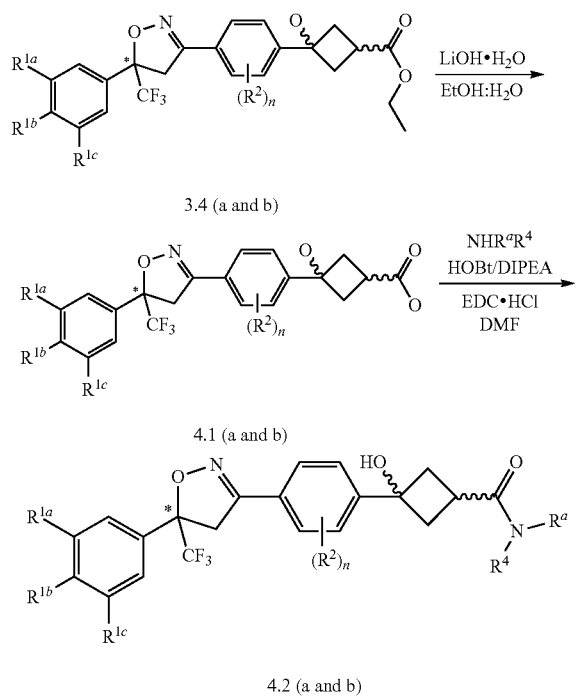

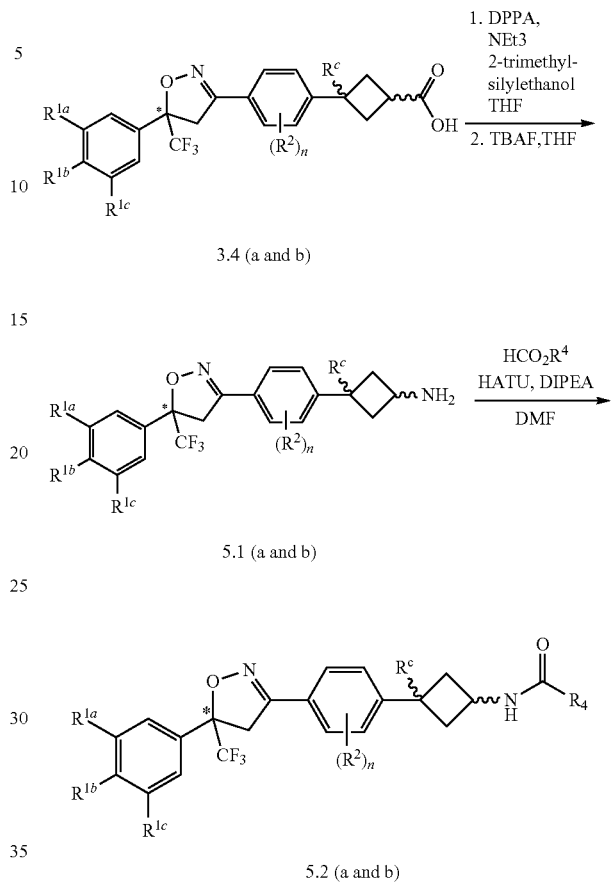

Alternatively, the hydroxycyclobutanones (3.4 a and b) can be carried on to the corresponding amides as shown in Scheme 4. The ester (3.4) can be hydrolyzed to the acid (4.1) with aqueous lithium hydroxide. At this point, the cis and trans isomers can be separated by chromatography. Amides (4.2a and 4.2b) can be prepared by coupling the acid (4.1a and 4.1b) with an amine using a condensing agent such as HATU or HOBt.

The phenyl cyclobutylamides can be prepared as shown in Scheme 5. Curtis rearrangement of carboxylic acid (3.4) using a suitable phosphoryl azide such as DPPA, in the presence of a suitable isocyanate trapping reagent such as 2-trimethylsilylethanol or tert-butanol in a suitable solvent such as THF, provides an intermediate silylcarbamate. Free amine (5.1) formation can be accomplished by treating the intermediate silylcarbamate with a suitable fluorine source such as TBAF. Amide (5.2) formation can be brought about by coupling a suitable carboxylic acid with amine (5.1) in the presence of a suitable amide coupling reagent such as HATU or EDCl along with a suitable base such as DIPEA or triethylamine in a suitable polar aprotic solvent such as DMF.

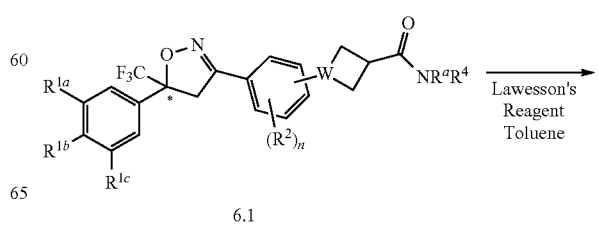

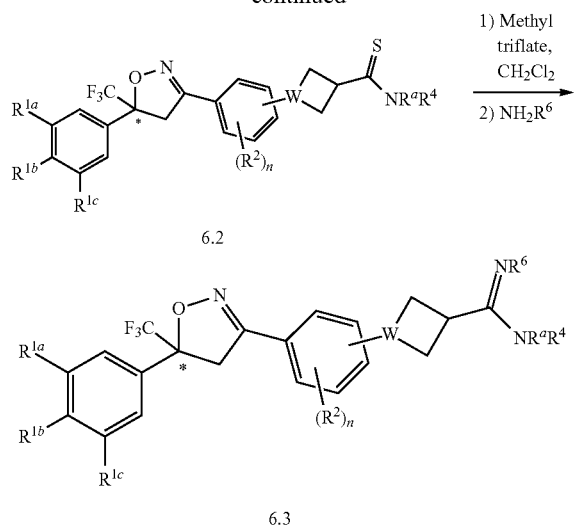

$R^{1a}$, $R^{1b}$, $R^{1c}$, $R^2$, $R^a$, $R^4$, and $n$ are as defined herein. The "*" represents a chiral center, e.g., "S" or "R" enantiomers.

Thioamide 6.2 can be prepared by treatment of amide 6.1 with Lawesson's reagent in refluxing toluene. Methyl triflate can be added to the thioamide 6.2 in a solvent such as $CH_2Cl_2$ to form a thioimidate intermediate as a solution. An amine in THF can be subsequently added directly to the thioimidate solution to afford the amidine derivatives 6.3.

One skilled in the art will recognize that, in some cases, after the introduction of a given reagent as it is depicted in the schemes, it may be necessary to perform additional routine synthetic steps not described in detail to complete the synthesis of Formula (1) compounds.

The present invention includes all veterinarily acceptable isotopically-labelled Formula (1) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{35}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", R C Larock, Wiley-VCH (1999 or later editions).

The Formula (1) compounds are useful as antiparasitic ectoparasitic agents, therefore, another embodiment of the present invention is a veterinary composition comprising a therapeutically effective amount of a Formula (1) compound, stereoisomer thereof, and a veterinarily acceptable excipient, diluent or carrier. The compounds of the present invention (including the compositions and processes used therein) may also be used in the manufacture of a medicament for the therapeutic applications described herein.

A typical formulation is prepared by mixing a Formula (1) compound with a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or veterinary composition thereof) or aid in the manufacturing of the veterinary product (i.e., medicament).

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). For example, the bulk drug substance (i.e., compound of the present invention or stabilized form of the compound (e.g., complex with a cyclodextrin derivative or other known complexation agent)) is dissolved in a suitable solvent in the presence of one or more other excipients. The compounds of the present invention are typically formulated into veterinary dosage forms to provide an easily controllable dosage form for administration.

The compounds may be administered alone or in a formulation appropriate to the specific use envisaged, the particular species of host animal or bird being treated and the parasite involved. Generally, they will be administered as a formulation in association with one or more veterinarily acceptable excipients, diluents, or carriers. The term "excipient", "diluent" or "carrier" is used herein to describe any ingredient other than the Formula (1) compounds or any additional antiparasitic agent. The choice of excipient, diluent, or carrier will to a large extent depend on factors such as the particular mode of administration, the effect of the excipient, carrier, or diluent on solubility and stability, and the nature of the dosage form.

The methods by which the compounds of the present invention may be administered include oral, topical, and subcutaneous administration. The preferred method of administration of the Formula (1) compounds is in an oral solid dosage form or oral liquid dosage form.

The Formula (1) compounds can be administered orally by capsule, bolus, tablet, powders, lozenges, chews, multi and nanoparticulates, gels, solid solution, films, sprays, or liquid form. This is a preferred method of administration and as such it is desirable to develop active Formula (1) compounds that are particularly suited to such formulations. Such formulations may be employed as fillers in soft or hard capsules and typically comprise a carrier, for example, water, ethanol, polyethylene glycol, N-methylpyrrolidone, propylene glycol, methylcellulose, or a suitable oil, and one or more emulsifying agents and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the active ingredient in a suitable medium. Oral formulations can comprise from about 0.5 mg/kg to 50 mg/kg of a Formula (1) compound, and preferably about 1 mg/kg to 30 mg/kg of a Formula (1) compound.

The compounds may be administered topically to the skin or mucosa, that is dermally or transdermally. This is a preferred method of administration and as such it is desirable to develop active Formula (1) compounds that are particularly suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the Formula (1) compounds have increased persistence of action and are more durable, for example they may be more water fast. Topical formulations of the combination contemplated herein can comprise from about 0.5 mg/kg to 50 mg/kg of a Formula (1) compound, and preferably about 1 mg/kg to 10 mg/kg of a Formula (1) compound.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinarily acceptable amount of a compound of the present invention alone, or with a veterinarily acceptable excipient, diluent, or carrier, and optionally an additional veterinary agent, or veterinarily acceptable salt thereof.

The compositions suitable for spot-on application according to the invention can be prepared by conventional mixing means. The volume of the applied composition can be from about 0.5 mL/kg to 5 mL/kg and preferably from about 1 mL/kg to 3 mL/kg.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA).

Certain topical formulations may include unpalatable additives to minimize oral exposure.

Subcutaneous injectable formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the instant invention alone or with an additional veterinary agent in the liquid carrier such that the final formulation contains from about 0.01 to 10% by weight of the active ingredients.

Suitable devices for subcutaneous administration include needle (including micro needle) injectors, needle-free injectors and infusion techniques. Subcutaneous formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of subcutaneous formulations under sterile conditions, for example, by lyophilisation, may readily be accomplished using standard veterinary techniques well known to those skilled in the art. The solubility of compounds of Formula (1) used in the preparation of subcutaneous solutions may be increased by the use of appropriate formulation techniques, such as the incorporation of solubility-enhancing agents.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

As described herein, compounds of the present invention may be administered alone or in combination with at least one additional veterinary agent including insecticides, acaricides, anthelmintics, fungicides, nematocides, antiprotozoals, bactericides, and growth regulators to form a multi-component agent giving an even broader spectrum of veterinary utility. Thus, the present invention also pertains to a composition comprising an effective amount of a Formula (1) compound, a stereoisomer thereof, and an effective amount of at least one additional veterinary agent and can further comprise one or more of a veterinarily acceptable excipient, diluent, or carrier.

The following list of additional veterinary agents together with which the compounds of the present invention can be used is intended to illustrate the possible combinations, but not to impose any limitation. Non-limiting examples of additional veterinary agents include: amitraz, arylpyrazoles as recited in publications WO1998/24767 and WO2005/060749, amino acetonitriles, anthelmintics (e.g., albendazole, cambendazole, fenbendazole, flubendazole, mebendazole, octadepsipeptides, oxfendazole, oxibendazole, paraherquamide, parbendazole, piperazines, praziquantel, thiabendazole, tetramisole, triclabendazole, levamisole, pyrantel pamoate, oxantel, morantel, and the like), avermectins (e.g., abamectin, doramectin, emamectin, eprinomectin, ivermectin, moxidectin, selamectin, and the like), milbemycin, milbemycin oxime, DEET, demiditraz, diethylcarbamazine, fipronil, insect growth regulators (e.g., hydroprene, kinoprene, methoprene, and the like), metaflumizone, niclosamide, permethrin, pyrethrins, pyriproxyfen, spinosad, and the like. In certain instances, combinations of a Formula (1) compound with an additional veterinary agent(s) can result in a greater-than-additive effect. Reducing the quantity of active ingredients released in the environment while ensuring effective pest control is always desirable.

It may be desirable to administer a compound of the present invention, stereoisomers thereof, alone or in a composition comprising a veterinarily acceptable excipient, diluent, or carrier, for example, for the purpose of treating a particular parasitic infection or infestation or condition associated therewith. It is within the scope of the present invention that two or more veterinary compositions, at least one of which contains a Formula (1) compound in accordance with the invention, and the other, an additional veterinary agent, may conveniently be combined in the form of a kit suitable for coadministration of the compositions.

The compounds of the present invention (including the compositions and processes used therein) may also be used in the manufacture of a medicament for the therapeutic applications described herein.

The compounds of the present invention, stereoisomers thereof, and compositions comprising a therapeutically effective amount of a Formula (1) compound and a veterinarily acceptable excipient, diluent, or carrier are useful as ectoparasiticides for the control and treatment of infections or infestations manifested by said ectoparasite in an animal. The compounds of the present invention have utility as an ectoparasiticide, in particular, as an acaricide and insecticide. They may, in particular, be used in the fields of veterinary medicine, livestock husbandry and the maintenance of public health: against acarids, insects, and copepods which are parasitic upon vertebrates, particularly warm-blooded vertebrates, including companion animals, livestock, and fowl and cold-blooded vertebrates like fish. Some non-limiting examples of acaride, insect, and copepod parasites include: ticks (e.g., *Ixodes* spp., *Rhipicephalus* spp., *Boophilus* spp., *Amblyomma* spp., *Hyalomma* spp., *Haemaphysalis* spp., *Dermacentor* spp., *Ornithodorus* spp., and the like); mites (e.g., *Dermanyssus* spp., *Sarcoptes* spp., *Psoroptes* spp., *Chorioptes* spp., *Demodex* spp., and the like); chewing and sucking lice (e.g., *Damalinia* spp., *Linognathus* spp., and the like); copepods (e.g., sea lice within the Order Siphonostomatoida, including genera Lepeophtheirus and Caligus); fleas (e.g., *Siphonaptera* spp., *Ctenocephalides* spp., and the like); biting flies and midges (e.g., *Tabanidae* spp., *Haematobia* spp., *Stomoxys* spp., *Dermatobia* spp., *Simuliidae* spp., *Ceratopogonidae* spp., *Psychodidae* spp., and the like); and bed bugs (e.g., insects within the genus *Cimex* and family Cimicidae).

The compounds of the present invention and compositions comprising compounds of the present invention in conjunction with at least one other veterinary agent are of particular value in the control of ectoparasites, endoparasites, and insects which are injurious to, or spread or act as vectors of diseases in companion animals, livestock, birds, and fish. The ectoparasites, insects, and endoparasites which can be treated with a combination of a Formula (1) compound and an additional veterinary agent include those as herein before described and including helminthes of the phylum platyhelminthes (e.g., trematodes, eucestoda, and cestoda), and nemathelminthes (e.g., nematodes).

Any of the compounds of the present invention, or a suitable combination of a compound of the present invention and optionally, with at least one additional veterinary agent may be administered directly to the animal or bird and/or indirectly by applying it to the local environment in which the animal or bird dwells (such as bedding, enclosures, and the like). Direct administration includes contacting the skin, fur, or feathers of a subject animal or bird with the compound(s), or by feeding or injecting the compounds into the animal or bird.

The Formula (1) compounds, stereoisomers thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily acceptable excipient, diluent, or carrier, to animals in good health comprising the application to said animal to reduce or eliminate the potential for human parasitic infection or infestation from parasites carried by the animal and to improve the environment in which the animals inhabit.

The reactions set forth herein can be done generally under a positive pressure of argon or nitrogen or with a drying tube, at ambient temperature (unless otherwise stated), in anhydrous solvents, and the reaction flasks fitted with rubber septa for the introduction of substrates and reagents via syringe. Glassware is oven dried and/or heat dried. Analytical thin layer chromatography (TLC) can be performed using glass-backed silica gel 60 F 254 precoated plates and eluted with appropriate solvent ratios (v/v). Reactions can be assayed by TLC or LCMS and terminated as judged by the consumption of starting material. Visualization of the TLC plates can be done with UV light (254 nM wavelength) or with an appropriate TLC visualizing solvent and activated with heat. Flash column chromatography (Still et al., *J. Org. Chem.* 43, 2923, (1978) can be performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

One skilled in the art will also recognize that Formula (1) compounds and the intermediates described herein can be subjected to various electrophilic, nucleophilic, radical, organometallic, oxidation, and reduction reactions to add substituents or modify existing substituents.

EXAMPLES

The following examples were prepared in a manner as described in the Schemes above.

Preparation 1

3-(4-diethoxymethyl-phenyl)-3-hydroxy-cyclobutanecarboxylic acid ethyl ester

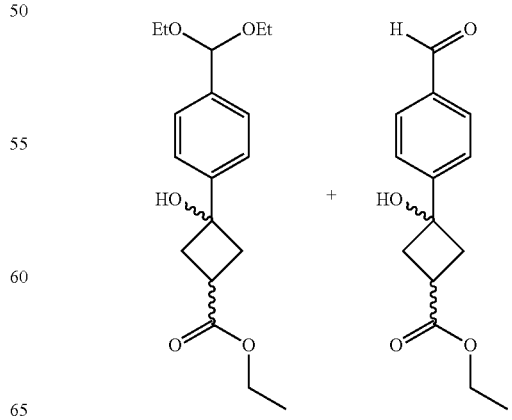

To a stirred suspension of magnesium (2.70 g, 112.67 mmol) in THF (300 mL) was added 1,2 dibromoethane (3.25 g, 17.32 mmol) followed by 1-bromo-4-diethoxymethyl-benzene (18 g, 73.23 mmol) at 75° C. for generation of Grignard reagent. Magnesium dissolved completely and reaction mixture turned brown. Reaction mixture was cooled to −10° C. and was added to pre-dissolved solution of 3-oxo-cyclobutanecarboxylic acid ethyl ester (8 g, 56.33 mmol) in THF (150 mL) at −10° C. Resulting reaction mixture was stirred at room temperature for 2 hours under nitrogen atmosphere. After complete consumption of starting material, reaction mixture was quenched with saturated solution of ammonium chloride (150 mL). Aqueous layer was extracted with EtOAc (3×150 mL). Combined organic layers were dried over sodium sulphate; filtered and evaporated in vacuo to afford crude residue. Crude was purified by column chromatography on silica gel (100-200 mesh size). Compound was eluted in 15% ethyl acetate in hexane to afford acetal as yellowish oil (7 g) and aldehyde was also obtained (2 g). $^1$H NMR (400 MHz, CDCl$_3$) δ: Mixture of aldehyde and acetal: 1.22 (t, 6H, J=7.04 Hz), 1.27 (t, 3H, J=7.14 Hz), 2.58-2.62 (m, 2H), 2.82-2.89 (m, 3H), 3.02 (s, 1H), 3.48-3.63 (m, 4H), 4.17 (q, 2H, J=7.12 Hz), 5.48 (s, 1H), 7.46-7.50 (m, 4H).

Preparation 2

3-hydroxy-3-[4-(hydroxyimino-methyl)phenyl]-cyclobutane carboxylic acid ethyl ester

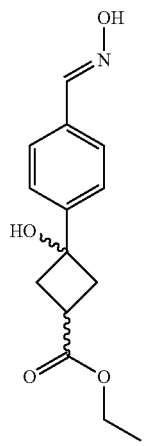 [SMILES: CCOC(=O)C1CC(O)(c2ccc(/C=N/O)cc2)C1]

To a solution of 3-(4-Diethoxymethyl-phenyl)-3-hydroxy-cyclobutanecarboxylic acid ethyl ester (Preparation 1, 7 g, 21.73 mmol) in EtOH:H$_2$O (80 mL, 1:1) was added sodium acetate (3.2 g, 39.31 mmol) followed by hydroxylamine hydrochloride (2.24 g, 32.60 mmol) at 0° C. Resulting reaction mixture was stirred at room temperature for 16 hours. After consumption of starting material, reaction mixture was concentrated in vacuo and diluted with water (70 mL). Aqueous layer was extracted with EtOAc (3×70 mL). Combined organic layer was dried over sodium sulphate, filtered and evaporated under reduced pressure to afford crude residue. Crude was purified by column chromatography on silica gel (100-200 mesh size). Compound was eluted using 40% ethyl acetate in hexane to afford yellowish oil (4.7 g, 87%). $^1$H NMR and LC-MS was consistent. $^1$H NMR (400 MHz, DMSO-d6) δ: 1.19 (t, J=7.16 Hz, 3H), 2.60-2.65 (m, 2H), 2.78-2.82 (m, 1H), 4.07 (q, J=7.1 Hz, 2H), 7.50-7.50 (m, 4H), 8.12 (s, 1H), 11.18 (s, 1H). LCMS (m/z): 246.10 (M+H).

Preparation 3

3-hydroxy-3-{4-[5-(3,4,5-trichloro-phenyl)-5-trifluoromethyl-4,5-dihydro-isoxazol-3-yl]-phenyl}-cyclobutanecarboxylic acid ethyl ester

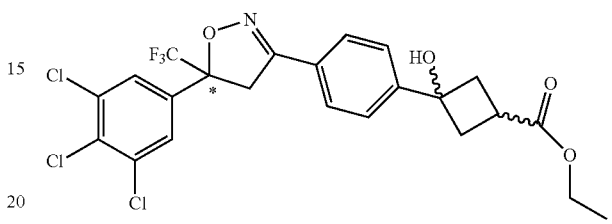

To a stirred solution of 3-hydroxy-3-[4-(hydroxyiminomethyl)-phenyl]-cyclobutane carboxylic acid ethyl ester (Preparation 2, 4.7 g, 17.87 mmol) in DMF (10 mL) was added N-chloro succinimide (2.61 g, 19.65 mmol) and heated at 50° C. for 1 hour. After complete consumption of starting material, reaction was cooled to 0° C., potassium hydrogen carbonate (2.68 g, 26.88 mmol) was added followed by addition of pre dissolved solution of 1,2,3-trichloro-5-(1-trifluoromethyl-vinyl)-benzene (5.40 g, 19.65 mmol). Resulting reaction mixture was stirred at room temperature for 16 hours. After consumption of chloro intermediate, reaction mixture was diluted with EtOAc (50 mL), washed with water (5×30 mL), dried over anhydrous sodium sulphate and concentrated in vacuo. Purification was done by column chromatography (silica gel, 100-200 mesh). Compound was eluted using 15% ethyl acetate in hexane as eluent to afford white sticky solid (4.7 g, 49%). $^1$H NMR (400 MHz, CDCl$_3$) δ 1.28 (t, J=9.36 Hz, 3H), 2.57-2.62 (m, 2H), 2.83-2.90 (m, 3H), 3.68 (d, J=17.28 Hz, 1H), 4.08 (d, J=17.16 Hz, 1H), 4.20 (q, J=7.2 Hz, 2H), 7.55-7.57 (m, 2H), 7.64-7.67 (m, 4H). LC-MS (m/z): 536.10 (M−H).

Preparation 4

3-hydroxy-3-{4-[5-(3,4,5-trichloro-phenyl)-5-trifluoromethyl-4,5-dihydro-isoxazol-3-yl]-phenyl}-cyclobutanecarboxylic acid

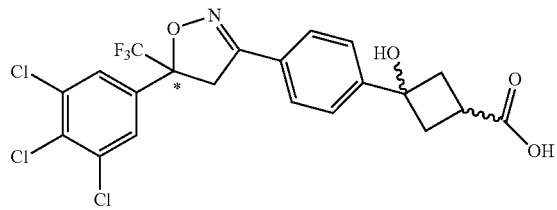 [SMILES: O=C(O)C1CC(O)(c2ccc(C3=NOC(c4cc(Cl)c(Cl)c(Cl)c4)(C(F)(F)F)C3)cc2)C1]

To a stirred solution of 3-hydroxy-3-[4-(hydroxyiminomethyl)-phenyl]-cyclobutane carboxylic acid ethyl ester (Preparation 3, 1.2 g, 2.24 mmol) in EtOH:H$_2$O (1:1, 80 mL) was added lithium hydroxide (0.471 g, 11.24 mmol) at 0° C. Resulting reaction mixture was stirred at room temperature for 16 hours. After consumption of starting material, reaction mixture was concentrated in vacuo, suspension was diluted with water (10 mL) and acidified with 1M HCl up to pH=2 at 0° C., solid was precipitated out. Resulting solid was filtered on Whatmann filter paper. Solid was dissolved in EtOAc (20 mL), dried over sodium sulphate, filtered and evaporated to afford solid. Solid was dissolved in DCM (2 mL) and precipitated with n-pentane (10 mL). Solid was filtered and dried to afford white solid (0.575 g, 51%). $^1$H NMR (400 MHz, DMSO-d$_6$) δ: 2.50-2.53 (m, 2H), 2.56-2.62 (m, 2H), 2.71-2.79 (m, 1H), 4.27-4.39 (m, 2H), 7.63 (d, 2H, J=8.52 Hz), 7.70 (d, 2H, J=8.40 Hz), 7.85 (s, 2H), 12.19 (bs, 1H); LC-MS (m/z): 506.00 (M−H).

Example 1

3-hydroxy-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide

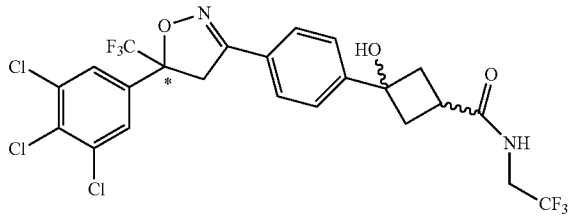

To a stirred solution of 3-hydroxy-3-{4-[5-(3,4,5-trichloro-phenyl)-5-trifluoromethyl-4,5-dihydro-isoxazol-3-yl]-phenyl}-cyclobutanecarboxylic acid (Preparation 4, 0.050 g, 0.098 mmol) in DMF (0.5 mL) was added HOBt (0.013 g, 0.096 mmol), DIPEA (0.025 g, 0.193 mmol) EDCl.HCl (0.019 g, 0.099 mmol) and 2,2,2-Trifluoro-ethylamine hydrochloride (0.013 g, 0.096 mmol) at 0° C. Resulting reaction mixture was stirred at room temperature for 18 h under nitrogen atmosphere. After complete consumption of starting material, reaction mixture was quenched with water (5 mL) and extracted with EtOAc (2×5 mL). Combined organic layer was washed with brine (5 mL), dried over sodium sulphate and evaporated in vacuo to get thick oil, 0.093 mg crude. Crude was purified by column chromatography on silica gel (100-200 mesh size). Compound was eluted using 2% methanol in DCM to afford thick yellow oil, which was re-purified by DCM in pentane (1:9) to afford white solid (0.020 g, 37.5%). $^1$H-NMR (400 MHz, CDCl$_3$) δ: 2.55-2.57 (m, 2H), 2.87-2.91 (m, 3H), 3.67 (d, 1H, J=17.24), 3.96-4.01 (m, 2H), 4.08 (d, 1H, J=17.2 Hz), 4.71 (s, 1H), 5.97 (t, 1H, J=6.32 Hz), 7.55 (d, 2H, J=8.44 Hz), 7.64-7.6 (m, 4H). LC-MS (m/z): [M−H] 586.90.

Example 2

3-hydroxy-3-{4-[5-(3,4,5-trichloro-phenyl)-5-trifluoromethyl-4,5-dihydro-isoxazol-3-yl]-phenyl}-cyclobutanecarboxylic acid cyclopropylamide

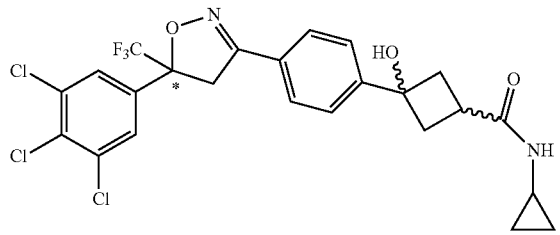 [SMILES: O=C(NC1CC1)C1CC(O)(c2ccc(C3=NOC(c4cc(Cl)c(Cl)c(Cl)c4)(C(F)(F)F)C3)cc2)C1]

To a stirred solution of 3-hydroxy-3-{4-[5-(3,4,5-trichloro-phenyl)-5-trifluoromethyl-4,5-dihydro-isoxazol-3-yl]-phenyl}-cyclobutanecarboxylic acid (Preparation 4, 0.1 g, 0.196 mmol) in DMF (3 mL) was added DIPEA (0.051 g, 0.393 mmol), HOBt (0.027 g, 0.196 mmol), EDCl.HCl (0.057 g, 0.294 mmol) and cyclopropyl amine (0.011 g, 0.196 mmol) at 0° C. Resulting reaction mixture was stirred at room temperature for 16 hours under nitrogen atmosphere. After complete consumption of starting material, reaction mixture was quenched with water (50 mL) and extracted with EtOAc (5×20 mL). Combined organic layer was washed with saturated NaHCO$_3$ (2×50 mL), dried over sodium sulphate and evaporated in vacuo to get 0.2 g (crude). Crude was purified by column chromatography on silica gel (100-200 mesh). Compound was eluted using 0.7% methanol in DCM to afford off white solid (0.055 g, 51%. $^1$H-NMR (400 MHz, CDCl$_3$) δ: 0.54-0.59 (m, 2H), 0.81-0.86 (m, 2H), 2.48-2.51 (m, 2H), 2.75-2.86 (m, 4H), 3.67 (d, 1H, J=17.16 Hz), 4.07 (d, 1H, J=17.16 Hz), 5.73 (s, 1H), 5.79 (bs, 1H), 7.54 (d, 2H, J=8.2 Hz), 7.62-7.63 (m, 4H); LC-MS (m/z): [M−H] 544.70, Example 3

3-hydroxy-3-{4-[5-(3,4,5-trichloro-phenyl)-5-trifluoromethyl-4,5-dihydro-isoxazol-3-yl]-phenyl}-cyclobutanecarboxylic acid methylamide

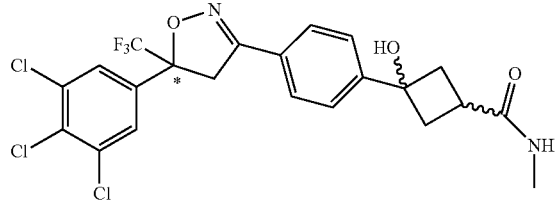 [SMILES: CNC(=O)C1CC(O)(c2ccc(C3=NOC(c4cc(Cl)c(Cl)c(Cl)c4)(C(F)(F)F)C3)cc2)C1]

To a stirred solution of 3-hydroxy-3-{4-[5-(3,4,5-trichloro-phenyl)-5-trifluoromethyl-4,5-dihydro-isoxazol-3-yl]-phenyl}-cyclobutanecarboxylic acid (Preparation 4, 0.060 g, 0.118 mmol) in dry DMF (1 mL) was added HATU (0.067 g, 0.177 mmol), HOBt (0.0175 g, 0.129 mmol), DIPEA (0.03 g, 0.236 mmol) and saturated solution of methyl amine in THF (2 mL) at 0° C. Resulting reaction mixture was stirred 0° C. for 2 hours and at room temperature for 18 hours. After complete consumption of starting material, reaction mixture was quenched with water (5 mL), extracted with EtOAc (10 mL). Organic layer was washed with saturated solution of lithium chloride (2×20 mL), water (2×20 mL), dried over sodium sulphate and evaporated in vacuo to get brown crude. Crude was purified by column chromatography on silica gel (100-200 mesh size). Compound was eluted using 1.2% methanol in DCM to afford sticky mass, which was crystallized by chloroform:pentane (1:9) to afford white solid (0.018 g, 29%). ¹H-NMR (400 MHz, CDCl₃) δ: 2.49-2.52 (m, 2H), 2.81-2.83 (m, 2H), 2.84-2.86 (m, 1H), 2.88 (d, 3H, J=4.88 Hz), 3.67 (d, 1H, J=17.08 Hz), 4.07 (d, 1H, J=17.16 Hz), 5.67 (bs, 1H), 5.81 (s, 1H), 7.55 (d, 2H, J=8.4 Hz), 7.62-7.64 (m, 4H). LC-MS (m/z): [M−H] 518.80. HPLC purity: 98.48%.

Example 4

3-hydroxy-3-{4-[5-(3,4,5-trichloro-phenyl)-5-trifluoromethyl-4,5-dihydro-isoxazol-3-yl]-phenyl}-cyclobutanecarboxylic acid dimethylamide

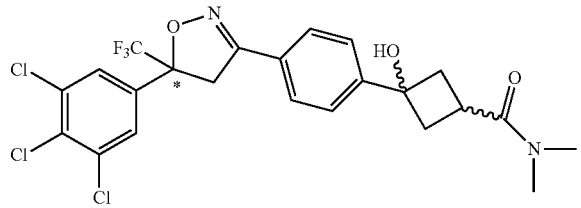 [SMILES: CN(C)C(=O)C1CC(O)(c2ccc(C3=NOC(c4cc(Cl)c(Cl)c(Cl)c4)(C(F)(F)F)C3)cc2)C1]

To a stirred solution of 3-hydroxy-3-{4-[5-(3,4,5-trichloro-phenyl)-5-trifluoromethyl-4,5-dihydro-isoxazol-3-yl]-phenyl}-cyclobutanecarboxylic acid (Preparation 4, 0.050 g, 0.098 mmol) in dry DMF (1 mL) was added HATU (0.056 g, 0.147 mmol), HOBt (0.014 g, 0.107 mmol), DIPEA (0.025 g, 0.196 mmol) and saturated solution of dimethyl amine in THF (2 mL) at 0° C. Resulting reaction mixture was stirred 0° C. for 1 hour and at room temperature for 18 hours. After complete consumption of starting material, reaction mixture was quenched with water (5 mL), extracted with EtOAc (10 mL). Organic layer was washed with saturated solution of lithium chloride (2×20 mL), brine (20 mL), dried over sodium sulphate and evaporated in vacuo to get crude. Crude was purified by column chromatography on silica gel (100-200 mesh size). Compound was eluted using 1.2% methanol in DCM to afford sticky mass, which was crystallized by chloroform:pentane (1:9) to afford white solid (0.029 g, 55%). ¹H-NMR (400 MHz, CDCl₃) δ: 2.53-2.57 (m, 2H), 2.79-2.88 (m, 2H), 3.02 (s, 6H), 3.27-3.31 (m, 1H), 3.67 (d, 1H, J=17.2 Hz), 4.08 (d, 1H, J=17.16 Hz), 5.04 (s, 1H), 7.57 (d, 2H, J=8.4 Hz), 7.64-7.65 (m, 4H); LC-MS (m/z): [M+H] 534.8.

Preparation 5

3-fluoro-3-{4-[5-(3,4,5-trichloro-phenyl)-5-trifluoromethyl-4,5-dihydro-isoxazol-3-yl]-phenyl}-cyclobutanecarboxylic acid ethyl ester

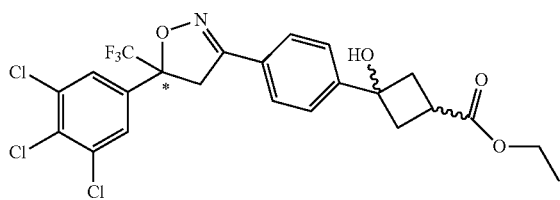 [SMILES: CCOC(=O)C1CC(O)(c2ccc(C3=NOC(c4cc(Cl)c(Cl)c(Cl)c4)(C(F)(F)F)C3)cc2)C1]

To a stirred solution of triethyl amine trihydrofluoride (4.21 g, 26.16 mmol, 4 eq.) in DCM (25 mL) was added triethyl amine (1.32 g, 13.08 mmol) in drop wise manner at −78° C. After 15 minutes was added X-TalFluoro-M (4.74 g, 19.62 mmol) followed by addition of pre-dissolved solution of 3-hydroxy-3-{4-[5-(3,4,5-trichloro-phenyl)-5-trifluoromethyl-4,5-dihydro-isoxazol-3-yl]-phenyl}-cyclobutanecarboxylic acid ethyl ester (Preparation 3, 3.5 g, 6.54 mmol) in DCM (15 mL) at −78° C. Resulting reaction mixture was stirred at room temperature for 16 hours. After consumption of starting material, reaction mixture was quenched with saturated aqueous solution of sodium bicarbonate (50 mL) and stirred at room temperature for 0.5 hours. Aqueous layer was extracted with DCM (3×50 mL). Combined organic layers were dried over sodium sulphate, filtered and evaporated. Purification was done by column chromatography on silica gel (100-200 mesh size). Compounds were eluted using 5% ethyl acetate in hexane to afford two off-white solids (2 g-non-polar spot, and 1.2 g-polar spot). ¹H NMR (400 MHz, CDCl₃) (Non Polar spot) δ: 1.26 (t, J=7.12 Hz, 3H), 2.80 (d, J=8.76 Hz, 2H), 2.87 (d, J=8.72 Hz, 2H), 3.47-3.49 (m, 1H), 3.67 (d, J=17.16 Hz, 1H), 4.08 (d, J=17.16 Hz, 1H), 4.16 (q, J=7.2 Hz, 2H), 7.51 (d, J=8.12 Hz, 2H), 7.63 (s, 2H), 7.67 (d, J=8.16 Hz, 2H); LC-MS (m/z): 536.00 (M−H).

¹H NMR (400 MHz, CDCl₃) (Polar spot) δ: 1.28 (t, J=7.1 Hz, 3H), 2.77-2.83 (m, 3H), 2.93-3.01 (m, 2H), 3.68 (d, J=17.08 Hz, 1H), 4.08 (d, J=17.20 Hz, 1H), 4.19 (q, J=7.12 Hz, 2H), 7.52 (d, J=8.44 Hz, 2H), 7.64 (d, J=8.240 Hz, 2H), 7.69 (d, J=8.20 Hz, 2H); LC-MS (m/z): 536.00 (M−H).

Preparation 6

3-fluoro-3-{4-[5-(3,4,5-trichloro-phenyl)-5-trifluoromethyl-4,5-dihydro-isoxazol-3-yl]-phenyl}-cyclobutanecarboxylic acid (non-polar spot)

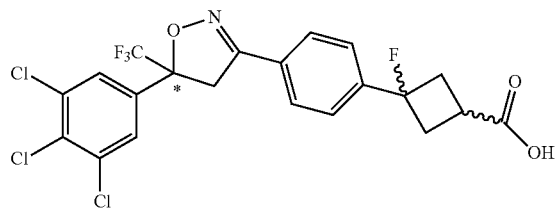 [SMILES: O=C(O)C1CC(F)(c2ccc(C3=NOC(c4cc(Cl)c(Cl)c(Cl)c4)(C(F)(F)F)C3)cc2)C1]

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid ethyl ester (non-polar compound from Preparation 5, 2 g, 3.72 mmol) in EtOH:H₂O (1:1, 140 mL) was added lithium hydroxide (0.782 g, 18.62 mmol) at 0° C. Resulting reaction mixture was stirred at room temperature for 16 hours. After consumption of starting material, reaction mixture was concentrated in vacuo; suspension was diluted with water (100 mL) and Acidified with 1M HCl up to pH=2 at 0° C. Solid was precipitated out, which was filtered on Whatmann filter paper. Solid was dissolved in EtOAc (100 mL), dried over sodium sulphate, filtered and evaporated to afford solid. Solid was washed with n-pentane (3×5 mL), dried to afford white solid (1.6 g, 85%). ¹H NMR (400 MHz, DMSO-d₆) δ: 2.75 (d, J=8.72 Hz, 2H), 2.81 (d, J=8.68 Hz, 2H), 3.37-3.39 (m, 1H), 4.29-4.41 (m, 2H), 7.55 (d, J=8.12 Hz, 2H), 7.77 (d, J=8.12 Hz, 2H), 7.84 (s, 2H), 12.50 (bs, 1H); LC-MS (m/z): 507.80 (M−H).

Preparation 7

3-fluoro-3-{4-[5-(3,4,5-trichloro-phenyl)-5-trifluoromethyl-4,5-dihydro-isoxazol-3-yl]-phenyl}-cyclobutanecarboxylic acid (polar spot)

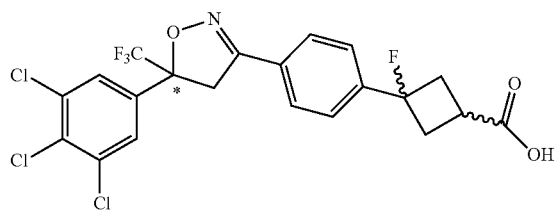 [SMILES: O=C(O)C1CC(F)(c2ccc(C3=NOC(c4cc(Cl)c(Cl)c(Cl)c4)(C(F)(F)F)C3)cc2)C1]

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid ethyl ester (polar spot of Preparation 5, 1.2 g, 2.23 mmol) in EtOH:H$_2$O (1:1, 80 mL) was added lithium hydroxide (0.469 g, 11.17 mmol) at 0° C. Resulting reaction mixture was stirred at room temperature for 16 hours. After consumption of starting material, reaction mixture was concentrated in vacuo, diluted with water (50 mL) and acidified using 1M HCl up to pH=2 at 0° C., solid was precipitated out. Resulting solid was filtered on Whatmann filter paper. Solid was dissolved in EtOAc (50 mL), dried over sodium sulphate, filtered and evaporated to afford solid, which was washed with n-pentane (3×3 mL) to afford white solid (0.820 g, 72%). $^1$H NMR (400 MHz, DMSO-d$_6$) δ: 2.75-2.84 (m, 5H), 4.30-4.42 (m, 2H), 7.65 (d, J=8.20 Hz, 2H), 7.77 (d, J=8.16 Hz, 2H), 7.85 (s, 2H), 12.52 (bs, 1H); LC-MS (m/z): 507.90 (M−H).

Example 5

3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide

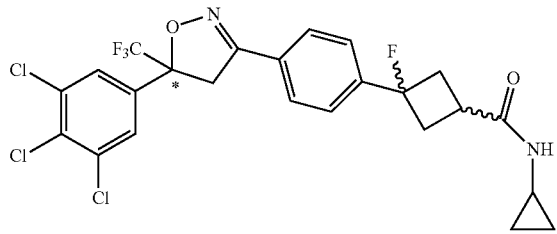 [SMILES: O=C(NC1CC1)C1CC(F)(c2ccc(C3=NOC(c4cc(Cl)c(Cl)c(Cl)c4)(C(F)(F)F)C3)cc2)C1]

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid (Preparation 6, 0.080 g, 0.156 mmol) in DMF (2 mL) was added HOBt (0.022 g, 0.156 mmol), DIPEA (0.040 g, 0.302 mmol) followed by addition of EDCl.HCl (0.045 g, 0.256 mmol) and cyclopropyl amine (0.009 g, 0.156 mmol) at 0° C. Resulting reaction mixture was stirred at room temperature for 18 hours under nitrogen atmosphere. After complete consumption of starting material, reaction mixture was quenched with water (10 mL), extracted with ethyl acetate (2×10 mL). Combined organic layer was washed with brine (20 mL), lithium chloride solution (20 mL), water (20 mL), dried over sodium sulphate and evaporated in vacuo to get crude. Crude was purified by column chromatography on silica gel (100-200 mesh size). Compound was eluted using 1% methanol in DCM to afford thick yellow oil, which was re-purified by DCM in pentane (1:9) to afford white solid (0.035 g, 41%. $^1$H-NMR (400 MHz, CDCl$_3$) δ: 0.48-0.52 (m, 2H), 0.76-0.81 (m, 2H), 2.69-2.77 (m, 2H), 2.83-2.93 (m, 3H), 3.15-3.23 (m, 1H), 3.67 (d, 1H, J=17.2 Hz), 4.07 (d, 1H, J=17.2 Hz), 5.58 (bs, 1H), 7.56-7.58 (m, 2H), 7.64-7.66 (m, 4H). LC-MS (m/z): [M−H] 546.90.

Example 6

3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide

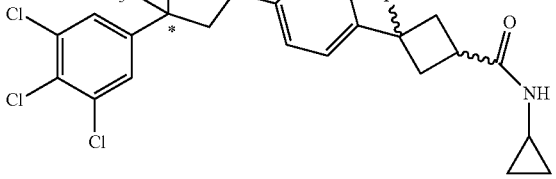

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid (Preparation 7, 0.1 g, 0.195 mmol) in DMF (3 mL) was added HOBt (0.026 g, 0.195 mmol), DIPEA (0.051 g, 0.391 mmol) followed by addition of EDCl.HCl (0.056 g, 0.293 mmol) and cyclopropyl amine (0.011 g, 0.195 mmol) at room temperature. Resulting reaction mixture was stirred at room temperature for 18 hours under nitrogen atmosphere. After complete consumption of starting material, reaction mixture was quenched with water (20 mL) and extracted with EtOAc (5×20 mL). Combined organic layer was washed with saturated water (100 mL), brine (100 mL), dried over sodium sulphate and evaporated in vacuo to get a yellow semisolid (0.108 g, crude). Crude was purified by column chromatography on silica gel (100-200 mesh). Compound was eluted using 0.5% methanol in DCM to afford off white solid (0.020 g, 19%, CR963-125249-74-1). $^1$H-NMR (400 MHz, CDCl$_3$) δ: 0.49-0.51 (m, 2H), 0.76-0.81 (m, 2H), 2.52-2.58 (m, 1H), 2.67-2.76 (m, 3H), 2.93-3.06 (m, 2H), 3.68 (d, 1H, J=17.04 Hz), 4.08 (d, 1H, J=17.16 Hz), 5.55 (bs, 1H), 7.51 (d, 2H, J=8.08 Hz), 7.63 (s, 2H), 7.68 (d, 2H, J=8.20 Hz); LC-MS (m/z): [M−H] 546.80.

Example 7

3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide

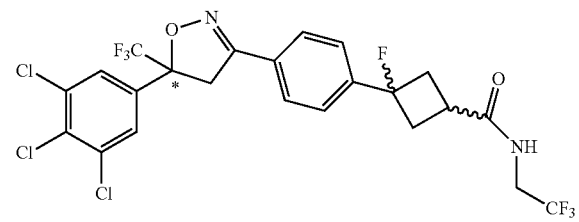 [SMILES: O=C(NCC(F)(F)F)C1CC(F)(c2ccc(C3=NOC(c4cc(Cl)c(Cl)c(Cl)c4)(C(F)(F)F)C3)cc2)C1]

To a stirred solution of 3-Fluoro-3-{4-[5-(3,4,5-trichloro-phenyl)-5-trifluoromethyl-4,5-dihydro-isoxazol-3-yl]-phenyl}-cyclobutanecarboxylic acid (Preparation 6, 0.1 g, 0.195 mmol) in DMF (3 mL) was added HOBt (0.027 g, 0.195 mmol) and DIPEA (0.050 g, 0.391 mmol) followed by addition of EDCl.HCl (0.056 g, 0.292 mmol) and 2,2,2-trifluoro-ethylamine hydrochloride (0.026 g, 0.195 mmol) at 0° C. Resulting reaction mixture was stirred at room temperature for 16 hours under nitrogen atmosphere. After complete consumption of starting material, reaction mixture was quenched with water (50 mL) and extracted with EtOAc (3×20 mL). Combined organic layer was washed with saturated NaHCO₃ (2×50 mL), dried over sodium sulphate and evaporated in vacuo to get 0.150 g crude. Crude was purified by column chromatography on silica gel (100-200 mesh size). Compound was eluted using 0.8% methanol in DCM to afford white solid (0.060 g, 52%). ¹H-NMR (400 MHz, CDCl₃) δ: 2.80-2.90 (m, 3H), 2.91-2.98 (m, 1H), 3.30-3.39 (m, 1H), 3.67 (d, 1H, J=17.16 Hz), 3.90-3.99 (m, 2H), 4.07 (d, 1H, J=17.16 Hz), 5.71 (bs, 1H), 7.53 (d, 2H, J=8.32 Hz), 7.64-7.67 (m, 4H); LC-MS (m/z): [M−H] 588.70.

Example 8

3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide

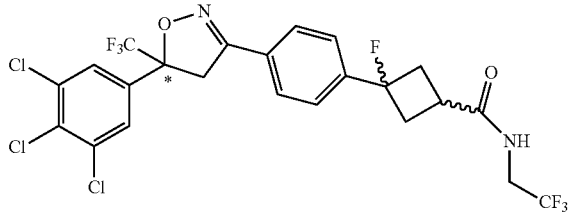

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid (Preparation 7, 0.1 g, 0.200 mmol) in DMF (3 mL) was added HOBt (0.026 g, 0.200 mmol), DIPEA (0.050 g, 0.392 mmol) followed by addition of EDCl.HCl (0.056 g, 0.294 mmol, 1.5 eq.) and 2,2,2-trifluoro-ethylamine hydrochloride (0.026 g, 0.200 mmol) at room temperature. Resulting reaction mixture was stirred at room temperature for 18 hours under nitrogen atmosphere. After complete consumption of starting material, reaction mixture was quenched with water (50 mL) and extracted with EtOAc (3×20 mL). Combined organic layer was washed with water (5×30 mL), brine (50 mL), saturated NaHCO₃ (50 mL), dried over sodium sulphate and evaporated in vacuo to get crude. Crude was purified by column chromatography on silica gel (100-200 mesh size). Compound was eluted using 1% methanol in DCM to afford sticky mass, which was crystallized with pentane to afford white solid (0.065 g, 56%). ¹H-NMR (400 MHz, CDCl₃) δ: 2.77-2.83 (m, 3H), 2.96-3.08 (m, 2H), 3.68 (d, 1H, J=17.2 Hz), 3.92-4.00 (m, 2H), 4.08 (d, 1H, J=17.2 Hz), 5.70 (t, 1H, J=6.3 Hz), 7.52 (d, 2H, J=8.2 Hz), 7.64 (s, 2H), 7.70 (d, 2H, J=8.12 Hz); LC-MS (m/z): [M−H] 588.60.

Example 9

3-fluoro-3-{4-[5-(3,4,5-trichloro-phenyl)-5-trifluoromethyl-4,5-dihydro-isoxazol-3-yl]-phenyl}-cyclobutanecarboxylic acid methylamide

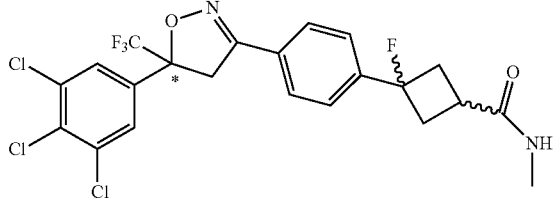 [SMILES: CNC(=O)C1CC(F)(c2ccc(C3=NOC(c4cc(Cl)c(Cl)c(Cl)c4)(C(F)(F)F)C3)cc2)C1]

To a stirred solution of 3-Fluoro-3-{4-[5-(3,4,5-trichloro-phenyl)-5-trifluoromethyl-4,5-dihydro-isoxazol-3-yl]-phenyl}-cyclobutanecarboxylic acid (Preparation 7, 0.1 g, 0.196 mmol) in DCM (2 mL) was added oxalyl chloride (0.023 g, 0.196 mmol) at 0° C. and stirred for 30 minutes under nitrogen atmosphere. After 30 minutes, reaction mixture was again cooled 0° C. and methyl amine (gas) was purged for 2 hours. Resulting reaction mixture was stirred at room temperature for 18 hours. After complete consumption of starting material, reaction mixture was quenched with water (20 mL) and extracted with DCM (3×20 mL). Combined organic layer was washed with saturated NaHCO₃ (2×50 mL), water (2×50 mL), brine (50 mL), dried over sodium sulphate and evaporated in vacuo to crude. Crude was purified by column chromatography on silica gel (100-200 mesh size). Compound was eluted using 1% methanol in DCM to afford sticky mass, which was crystallized by pentane to afford white solid (0.035 g, 34%). ¹H-NMR (400 MHz, CDCl₃) δ: 2.57-2.64 (m, 1H), 2.69-2.79 (m, 2H), 2.85 (d, 3H, J=4.84 Hz), 2.95-3.06 (m, 2H), 3.68 (d, 1H, J=17.12 Hz), 4.08 (d, 1H, J=17.2 Hz), 5.45 (bs, 1H), 7.52 (d, 2H, J=8.24 Hz), 7.63 (s, 2H), 7.69 (d, 2H, J=8.08 Hz); LC-MS (m/z): [M−H] 520.70.

Example 10

3-fluoro-3-{4-[5-(3,4,5-trichloro-phenyl)-5-trifluoromethyl-4,5-dihydro-isoxazol-3-yl]-phenyl}-cyclobutanecarboxylic acid methylamide

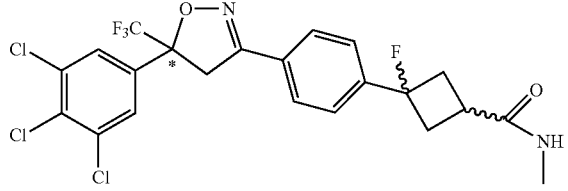 [SMILES: CNC(=O)C1CC(F)(c2ccc(C3=NOC(c4cc(Cl)c(Cl)c(Cl)c4)(C(F)(F)F)C3)cc2)C1]

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid (Preparation 6, 0.1 g, 0.196 mmol) in DCM (2 mL) was added oxalyl chloride (0.023 g, 0.193 mmol) at 0° C. and stirred for 1 hour under nitrogen atmosphere at room temperature. After 1 hour, reaction mixture was cooled to 0° C. and methyl amine (gas) was purged for 2 hours maintaining 0° C. Resulting reaction mixture was stirred at room temperature for 18 hours. After complete consumption of starting material, reaction mixture was diluted with DCM (3 mL), washed with water (3×3 mL).

Combined organic layer was washed with brine (5 mL), dried over sodium sulphate and evaporated in vacuo to get thick oil (0.070 g, crude). Crude was purified by column chromatography on silica gel (100-200 mesh). Compound was eluted using 2% methanol in DCM to afford sticky mass, which was re-purified by preparative TLC using 1.5% MeOH in DCM mobile phase to afford off white solid (0.030 g, 29%). $^1$H-NMR (400 MHz, CDCl$_3$) δ: 2.76-2.83 (m, 2H), 2.84 (d, 3H, J=4.88 Hz), 2.86-2.97 (m, 2H), 3.22-3.28 (m, 1H), 3.67 (d, 1H, J=17.08 Hz), 4.07 (d, 1H, J=17.20 Hz), 5.46 (bs, 1H), 7.57 (d, 2H, J=8.36 Hz), 7.64-7.66 (m, 4H); LC-MS (m/z): [M−H] 520.7.

Example 11

3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide

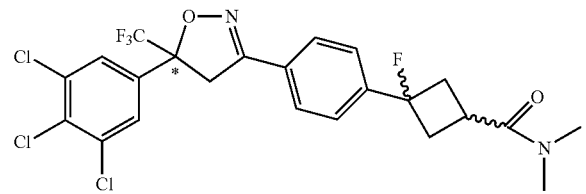 [SMILES: CN(C)C(=O)C1CC(F)(c2ccc(C3=NOC(c4cc(Cl)c(Cl)c(Cl)c4)(C(F)(F)F)C3)cc2)C1]

To a stirred solution of 3-Fluoro-3-{4-[5-(3,4,5-trichloro-phenyl)-5-trifluoromethyl-4,5-dihydro-isoxazol-3-yl]-phenyl}-cyclobutanecarboxylic acid (Preparation 6, 0.1 g, 0.196 mmol) in DCM (2 mL) was added oxalyl chloride (0.023 g, 0.193 mmol) at 0° C. Reaction mixture was stirred at room temperature for 1 hour and cooled to 0° C. followed by addition of dimethyl amine (gas) was purged for 2 hours. Resulting reaction mixture was stirred at room temperature for 18 hours. After complete consumption of starting material, reaction mixture was diluted with DCM (3 mL), washed with water (3×3 mL). Organic layer was dried over sodium sulphate and evaporated in vacuo to get crude thick oil (0.077 g). Crude was purified by column chromatography on silica gel (100-200 mesh size), compound was eluted using 2% methanol in DCM and crystallized with chloroform:pentane (1:9) to afford off white solid (0.035 g, 33%). $^1$H-NMR (400 MHz, CDCl$_3$) δ: 2.79-2.80 (m, 1H), 2.80-2.94 (m, 4H), 2.97 (s, 3H), 2.99 (s, 3H), 3.66-3.69 (m, 1H), 4.07 (d, 1H, J=17.16 Hz), 7.51 (d, 2H, J=8.16 Hz), 7.63-7.65 (m, 4H); LC-MS (m/z): [M−H] 535.0.

Example 12

3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide

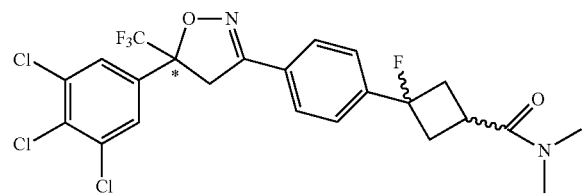 [SMILES: CN(C)C(=O)C1CC(F)(c2ccc(C3=NOC(c4cc(Cl)c(Cl)c(Cl)c4)(C(F)(F)F)C3)cc2)C1]

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid (Preparation 7, 0.085 g, 0.166 mmol) in DCM (4 mL) was added oxalyl chloride (0.025 g, 0.199 mmol) at 0° C. and stirred for 1 hour. After 1 hour, saturated solution of dimethyl amine in THF (4 mL) was added. Resulting reaction mixture was stirred at room temperature for 16 hours. After complete consumption of starting material, reaction mixture was concentrated in vacuo to afford crude. Crude was purified by column chromatography on silica gel (100-200 mesh size). Compound was eluted using 0.7% methanol in DCM to afford off white solid (0.026 g, 29%). $^1$H-NMR (400 MHz, CDCl$_3$) δ: 2.72-2.78 (m, 2H), 2.87-2.92 (m, 1H), 2.94 (s, 3H), 2.98 (s, 3H), 2.99-3.09 (m, 2H), 3.68 (d, 1H, J=17.2 Hz), 4.08 (d, 1H, J=17.16 Hz), 7.54 (d, 2H, J=8.16 Hz), 7.64 (s, 2H), 7.70 (d, 2H, J=8.24 Hz); LC-MS (m/z): [M−H] 534.60.

Example 13

3-fluoro-3-{4-[5-(3,4,5-trichloro-phenyl)-5-trifluoromethyl-4,5-dihydro-isoxazol-3-yl]-phenyl}-cyclobutanecarboxylic acid

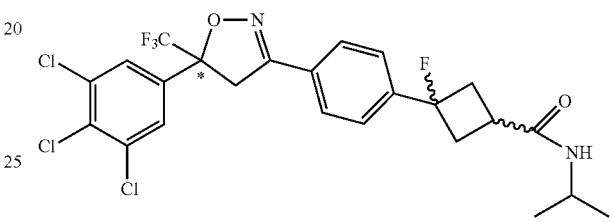

To a stirred solution of 3-fluoro-3-{4-[5-(3,4,5-trichloro-phenyl)-5-trifluoromethyl-4,5-dihydro-isoxazol-3-yl]-phenyl}-cyclobutanecarboxylic acid (Preparation 6, 0.2 g, 0.39 mmol) in dry DMF (3 mL) was added HATU (0.22 g, 0.58 mmol), HOBt (0.06 g, 0.43 mmol), DIPEA (0.102 g, 0.79 mmol.) and isopropyl amine (0.046 g, 0.78 mmol) at 0° C. Resulting reaction mixture was stirred at room temperature for 18 hours under nitrogen atmosphere. After complete consumption of starting material, reaction mixture was quenched with water (15 mL), extracted with EtOAc (2×30 mL). Organic layer was washed with saturated solution of lithium chloride (2×30 mL), brine (3×20 mL), dried over sodium sulphate and evaporated in vacuo to get crude. Crude was purified by column chromatography on silica gel (100-200 mesh size). Compound was eluted using 3% ethyl acetate in hexane to afford colorless sticky mass (0.170 g, 79%). $^1$H-NMR (400 MHz, CDCl$_3$) δ: 1.15 (d, 6H, J=6.52 Hz), 2.67-2.78 (m, 2H), 2.82-2.95 (m, 2H), 3.16-3.22 (m, 1H), 3.67 (d, 1H, J=17.2 Hz), 4.05-4.10 (m, 2H), 5.26 (bs, 1H), 7.57 (d, 2H, J=8.4 Hz), 7.64-7.66 (m, 4H); LC-MS (m/z): [M−H] 548.80.

Example 14

3-fluoro-3-{4-[5-(3,4,5-trichloro-phenyl)-5-trifluoromethyl-4,5-dihydro-isoxazol-3-yl]-phenyl}-cyclobutanecarboxylic acid ethylamide

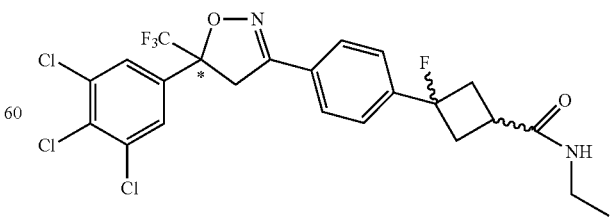

To a stirred solution of 3-Fluoro-3-{4-[5-(3,4,5-trichloro-phenyl)-5-trifluoromethyl-4,5-dihydro-isoxazol-3-yl]-phenyl}-cyclobutanecarboxylic acid (Preparation 6, 0.2 g, 0.391 mmol) in dry DMF (3 mL) was added HATU (0.223 g, 0.58 mmol), HOBt (0.06 g, 0.43 mmol), DIPEA (0.102 g, 0.79 mmol) and 2M solution of ethyl amine in THF (2 mL) at 0° C. Resulting reaction mixture was stirred at room temperature for 18 hours under nitrogen atmosphere. After complete consumption of starting material, reaction mixture was quenched with water (20 mL), extracted with EtOAc (2×30 mL). Combined organic layer was washed with brine (2×20 mL), saturated solution of lithium chloride (2×20 mL), water (20 mL), dried over sodium sulphate and evaporated in vacuo to get crude. Crude was purified by column chromatography on silica gel (100-200 mesh size). Compound was eluted using 1% methanol in DCM to afford off white solid (0.20 g, 64%). $^1$H-NMR (400 MHz, CDCl$_3$) δ: 1.15 (t, 3H, J=7.28 Hz), 2.67-2.78 (m, 2H), 2.84-2.96 (m, 2H), 3.22-3.26 (m, 1H), 3.28-3.35 (m, 2H), 3.67 (d, 1H, J=17.24 Hz), 4.07 (d, 1H, J=17.2 Hz), 5.43 (bs, 1H), 7.56 (d, 2H, J=8.36 Hz), 7.64-7.66 (m, 4H); LC-MS (m/z): [M−H] 535.00.

Example 15

3-fluoro-N-(2-oxo-2-((2,2,2-trifluoroethyl)amino)ethyl)-3-(4-(5-(3,4,5-trichlorophenyl)-5-(trifluoromethyl)-4,5-dihydroisoxazol-3-yl)phenyl)cyclobutanecarboxamide

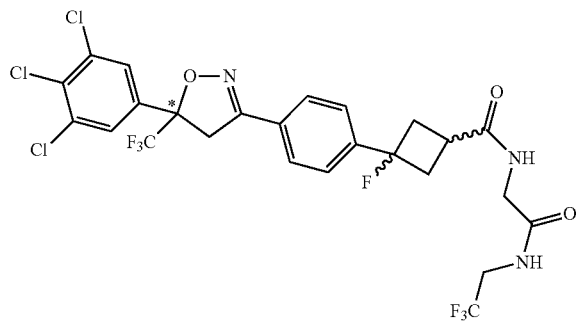 [SMILES: O=C(CNC(=O)C1CC(F)(c2ccc(C3=NOC(c4cc(Cl)c(Cl)c(Cl)c4)(C(F)(F)F)C3)cc2)C1)NCC(F)(F)F]

Prepared according to the procedures of Examples 5-15 using 2-amino-N-(2,2,2-trifluoroethyl)acetamide as a starting material the previous experimental was used to give the title compound (22.8 mg): m/z (Cl) 649.

Preparation 8

1-(4-formyl-phenyl)-azetidine-3-carboxylic acid

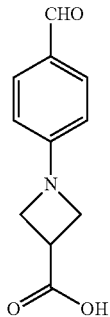

To a stirred solution of 4-fluoro benzaldehyde (5 g, 40.28 mmol) in DMSO (70 mL) was added azetidine-3-carboxylic acid (8.14 g, 80.56 mmol) followed by addition of triethyl amine (20.38 g, 201.41 mmol) at room temperature. Resulting reaction mixture was heated at 100° C. for 24 hours under nitrogen atmosphere. After complete consumption of starting material, reaction mixture was cooled to room temperature and quenched with ice cold water (150 mL). Aqueous layer was extracted with EtOAc (3×150 mL). Combined organic layer was washed with water (2×300 mL), dried over sodium sulphate; filtered and evaporated in vacuo to afford brown colored solid (4 g, 48%). $^1$H NMR (400 MHz, DMSO-d6) δ: 3.54-3.59 (m, 1H), 4.03 (t, 2H, J=6.8 Hz), 4.16 (t, 2H, J=8.36 Hz), 6.52 (d, 2H, J=8.36 Hz), 7.69 (d, 2H, J=8.6 Hz), 9.68 (s, 1H); LC-MS (M−H): =203.70

Preparation 9

1-(4-formyl-phenyl)-azetidine-3-carboxylic acid methyl ester

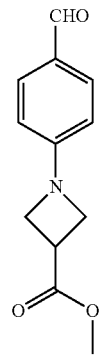

To a solution of 1-(4-Formyl-phenyl)-azetidine-3-carboxylic acid (Preparation 8, 4 g, 19.51 mmol) in DMF (50 mL) was added potassium carbonate (4.04 g, 29.77 mmol) at 0° C. and allowed to stir for 10 minutes followed by addition of methyl iodide (2.77 g, 19.51 mmol) at 0° C. Resulting reaction mixture was stirred at room temperature for 2 hours under nitrogen atmosphere. After consumption of starting material, reaction mixture was quenched with ice cold water (150 mL) and extracted with EtOAc (3×150 mL). Combined organic layer was washed with water (2×300 mL), brine (250 mL), dried over sodium sulphate and evaporated under reduced pressure to afford brown colored semi solid (4.7 g, crude). Crude was purified by column chromatography on silica gel (100-200 mesh). Compound was eluted using 20% ethyl acetate in hexane to afford yellow semisolid (2.6 g, 61%). $^1$H NMR (400 MHz, CDCl$_3$) δ: 3.58-3.62 (m, 1H), 3.76 (s, 3H), 4.15-4.22 (m, 4H), 6.42 (d, 2H, J=8.6 Hz), 7.72 (d, 2H, J=6.98 Hz), 9.74 (s, 1H); LC-MS (M+H): =220.20.

Preparation 10

1-[4-(hydroxyimino-methyl)-phenyl]-azetidine-3-carboxylic acid methyl ester

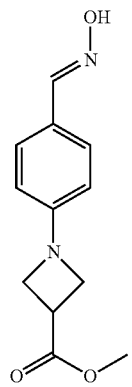 [SMILES: COC(=O)C1CN(c2ccc(/C=N/O)cc2)C1]

To a stirred suspension of 1-(4-formyl-phenyl)-azetidine-3-carboxylic acid methyl ester (Preparation 9, 2.6 g, 11.87 mmol) in methanol (25 mL) and water (25 mL) was added sodium acetate (1.75 g, 21.36 mmol) followed by hydroxylamine hydrochloride (1.24 g, 17.80 mmol) at 0° C. Resulting reaction mixture was stirred at room temperature for 3 hours. After consumption of starting material, methanol was evaporated under reduced pressure and extracted with EtOAc (4×30 mL). Combined organic layer was dried over anhydrous sodium sulphate and concentrated in vacuo to afford yellow colored solid (2.86 g, 99%). $^1$H NMR (400 MHz, CDCl$_3$) δ: 3.55-3.59 (m, 1H), 3.75 (s, 3H), 4.05-4.13 (m, 4H), 6.42 (d, 2H, J=8.56 Hz), 7.41 (d, 2H, J=8.6 Hz), 8.03 (s, 1H); LC-MS (M+H): =235.00.

Preparation 11

1-{4-[5-(3,4,5-trichloro-phenyl)-5-trifluoromethyl-4,5-dihydro-isoxazol-3-yl]-phenyl}-azetidine-3-carboxylic acid methyl ester

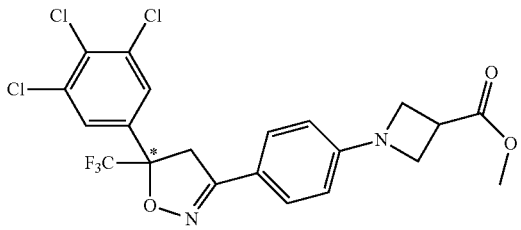 [SMILES: COC(=O)C1CN(c2ccc(C3=NOC(c4cc(Cl)c(Cl)c(Cl)c4)(C(F)(F)F)C3)cc2)C1]

To a stirred solution of 1-[4-(hydroxyimino-methyl)-phenyl]-azetidine-3-carboxylic acid methyl ester (Preparation 10, 2.36 g, 10.08 mmol) in DMF (25 mL) was added N-chloro succinimide (1.48 g, 11.09 mmol) at 0° C. Resulting reaction mixture was stirred at 0° C. for 1 hour and then at 10° C. for 1 hour. After complete consumption of starting material to chloro intermediate (red colored reaction mixture) potassium hydrogen carbonate (1.51 g, 15.12 mmol, 1.5 eq.) was added followed by of 1,2,3-trichloro-5-(1-trifluoromethyl-vinyl)benzene (1.21 g, 12.10 mmol) at room temperature. Resulting reaction mixture was stirred at room temperature for 4 hours under nitrogen atmosphere. After consumption of chloro intermediate, reaction mixture was quenched with water (200 mL) and extracted with EtOAc (2×200 mL). Combined organic layer was washed with water (2×400 mL), brine (2×200 mL), dried over anhydrous sodium sulphate and concentrated in vacuo to afford brown colored semi solid (2.5 g, crude). Crude compound was purified by column chromatography (silica gel, 100-200 mesh). Compound was eluted using 25% ethyl acetate in hexane to afford off white solid (1.91 g, 33%). $^1$H NMR (400 MHz, CDCl3): 3.58-3.63 (m, 2H), 3.75 (s, 3H), 4.03 (d, 1H, J=17.04 Hz), 4.07-4.15 (m, 4H), 6.39-6.42 (m, 2H), 7.46-7.49 (m, 2H), 7.63 (s, 2H); LC-MS (M+H): =506.90.

Preparation 12

1-{4-[5-(3,4,5-trichloro-phenyl)-5-trifluoromethyl-4,5-dihydro-isoxazol-3-yl]-phenyl}-azetidine-3-carboxylic acid

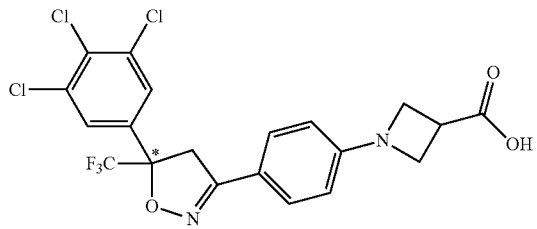 [SMILES: O=C(O)C1CN(c2ccc(C3=NOC(c4cc(Cl)c(Cl)c(Cl)c4)(C(F)(F)F)C3)cc2)C1]

To a stirred suspension of 1-{4-[5-(3,4,5-trichloro-phenyl)-5-trifluoromethyl-4,5-dihydro-isoxazol-3-yl]-phenyl}-azetidine-3-carboxylic acid methyl ester (Preparation 11, 1.91 g, 3.77 mmol) in THF:MeOH:H$_2$O (1:1:1, 60 mL) was added lithium hydroxide (0.791 g, 18.87 mmol) at room temperature and stirred at room temperature for 24 hours. After consumption of starting material, reaction mixture was concentrated in vacuo; suspension was diluted with water (20 mL) and acidified with 1N HCl up to pH ~4. Acidified aqueous layer was extracted with ethyl acetate (5×50 mL). Combined organic layer washed with brine (150 mL), dried over sodium sulphate and evaporated under reduced pressure to afford yellow semi solid, which was triturated with chloroform:n-pentane (1:9) to afford yellow solid (1.57 g, 85%). $^1$H NMR (400 MHz, DMSO) δ: 3.49-3.52 (m, 1H), 3.90 (t, 2H, J=6.7 Hz), 4.04 (t, 2H, J=8.12 Hz), 4.13-4.25 (m, 2H), 6.46 (d, 2H, J=8.64 Hz), 7.48 (d, 2H, J=8.6 Hz), 7.79 (s, 2H); LC-MS (M+H): =492.60.

Example 16

1-{4-[5-(3,4,5-trichloro-phenyl)-5-trifluoromethyl-4,5-dihydro-isoxazol-3-yl]-phenyl}-azetidine-3-carboxylic acid cyclopropylamide

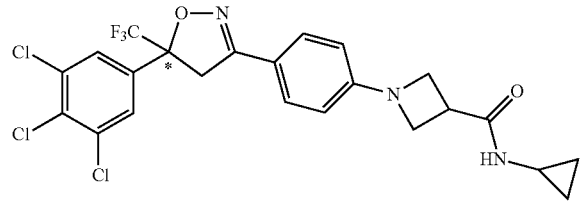 [SMILES: O=C(NC1CC1)C1CN(c2ccc(C3=NOC(c4cc(Cl)c(Cl)c(Cl)c4)(C(F)(F)F)C3)cc2)C1]

To a stirred solution of 1-{4-[5-(3,4,5-trichloro-phenyl)-5-trifluoromethyl-4,5-dihydro-isoxazol-3-yl]-phenyl}-azetidine-3-carboxylic acid (Preparation 12, 0.1 g, 0.203 mmol) in DMF (3 mL) was added HOBt (0.027 g, 0.203 mmol), DIPEA (0.052 g, 0.406 mmol), EDCl.HCl (0.058 g, 0.304 mmol) and cyclopropyl amine (0.011 g, 0.203 mmol) at 0° C. Resulting reaction mixture was stirred at room temperature for 16 hours under nitrogen atmosphere. After complete consumption of starting material, reaction mixture was quenched with water (20 mL) and extracted with EtOAc (3×20 mL). Combined organic layer was washed with saturated NaHCO$_3$ (2×50 mL), water (2×50 mL), brine (50 mL), dried over sodium sulphate and evaporated in vacuo to crude. Crude was purified by column chromatography on silica gel (100-200 mesh size).

Compound was eluted using 1.1% methanol in DCM to afford white solid (0.036 g, 33%). ¹H-NMR (400 MHz, CDCl₃) δ: 0.49-0.53 (m, 2H), 0.77-0.87 (m, 2H), 2.74-2.77 (m, 1H), 3.31-3.34 (m, 1H), 3.61 (d, 1H, J=16.88 Hz), 4.01-4.07 (m, 5H), 5.72 (bs, 1H), 6.40 (d, 2H, J=8.68 Hz), 7.47 (d, 2H, J=8.68 Hz), 7.63 (s, 2H). LC-MS (m/z): [M−H] 529.70.

Example 17

1-{4-[5-(3,4,5-trichloro-phenyl)-5-trifluoromethyl-4,5-dihydro-isoxazol-3-yl]-phenyl}-azetidine-3-carboxylic acid methylamide

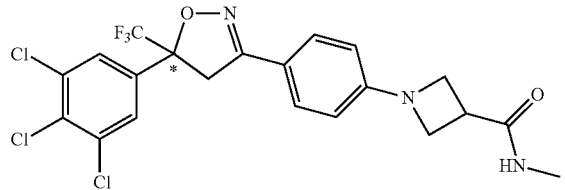 [SMILES: CNC(=O)C1CN(c2ccc(C3=NOC(c4cc(Cl)c(Cl)c(Cl)c4)(C(F)(F)F)C3)cc2)C1]

To a stirred solution of 1-{4-[5-(3,4,5-trichloro-phenyl)-5-trifluoromethyl-4,5-dihydro-isoxazol-3-yl]-phenyl}-azetidine-3-carboxylic acid (Preparation 12, 0.1 g, 0.203 mmol) in DCM (4 mL) was added oxalyl chloride (0.030 g, 0.0.243 mmol) at 0° C. and stirred for 1 hour under nitrogen atmosphere at room temperature. After 1 hour, saturated solution of methyl amine (4 mL) was added. Resulting reaction mixture was stirred at room temperature for 16 hours. After complete consumption of starting material, reaction mixture was concentrated in vacuo to get crude. Crude was purified by column chromatography on silica gel (100-200 mesh). Compound was eluted using 0.7% methanol in DCM to afford pale yellow solid (0.055 g, 54%). ¹H-NMR (400 MHz, CDCl₃) δ: 2.86-2.90 (d, 3H, J=4.84 Hz), 3.36-3.39 (m, 1H), 3.61 (d, 1H, J=17 Hz), 4.01-4.09 (m, 5H), 5.62-5.63 (m, 1H), 6.40-6.42 (m, 2H), 7.46-7.50 (m, 2H), 7.63 (s, 2H); LC-MS (m/z): [M−H] 503.80. HPLC purity: 96.77%.

Example 18

1-{4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide

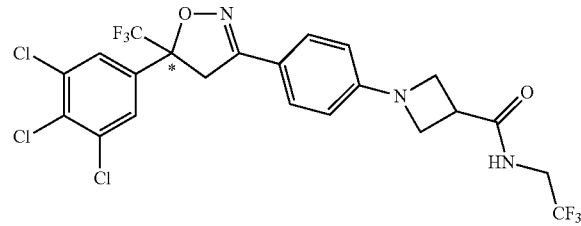 [SMILES: O=C(NCC(F)(F)F)C1CN(c2ccc(C3=NOC(c4cc(Cl)c(Cl)c(Cl)c4)(C(F)(F)F)C3)cc2)C1]

To a stirred solution of 1-{4-[5-(3,4,5-trichloro-phenyl)-5-trifluoromethyl-4,5-dihydro-isoxazol-3-yl]-phenyl}-azetidine-3-carboxylic acid (Preparation 12, 0.1 g, 0.203 mmol) in DMF (3 mL) was added DIPEA (0.052 g, 0.406 mmol), HOBt (0.027 g, 0.203 mmol), EDCl.HCl (0.058 g, 0.304 mmol) and 2,2,2-trifluoro-ethylamine hydrochloride (0.027 g, 0.203 mmol) at 0° C. Resulting reaction mixture was stirred at room temperature for 16 hours under nitrogen atmosphere. After complete consumption of starting material, reaction mixture was quenched with water (50 mL), extracted with EtOAc (3×20 mL). Combined organic layer was washed with saturated NaHCO₃ (2×50 mL), dried over sodium sulphate and evaporated in vacuo to get 0.170 mg crude. Crude was purified by column chromatography on silica gel (100-200 mesh size). Compound was eluted using 0.8% methanol in DCM to afford pale yellow solid, which was re-purified by DCM in pentane (1:9) to afford pale yellow solid (0.082 g, 71%). ¹H-NMR (400 MHz, CDCl₃) δ: 3.43-3.48 (m, 1H), 3.62 (d, 1H, J=17.04), 3.93-4.00 (m, 2H), 4.04 (d, 1H, J=17.0), 4.09-4.14 (m, 4H), 5.94 (t, 1H, J=6.06 Hz), 6.43 (d, 2H, J=8.72 Hz), 7.47-7.50 (m, 2H), 7.63 (s, 2H); LC-MS (m/z): [M−H] 571.70.

Example 19

1-{4-[5-(3,4,5-trichloro-phenyl)-5-trifluoromethyl-4,5-dihydro-isoxazol-3-yl]-phenyl}azetidine-3-carboxylic acid dimethylamide

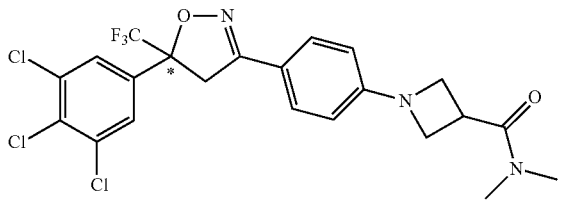 [SMILES: CN(C)C(=O)C1CN(c2ccc(C3=NOC(c4cc(Cl)c(Cl)c(Cl)c4)(C(F)(F)F)C3)cc2)C1]

To a stirred solution of 1-{4-[5-(3,4,5-Trichloro-phenyl)-5-trifluoromethyl-4,5-dihydro-isoxazol-3-yl]-phenyl}-azetidine-3-carboxylic acid (Preparation 12, 0.1 g, 0.203 mmol) in DMF (3 mL) was added HATU (0.115 g, 0.304 mmol) HOBt (0.03 g, 0.223 mmol), DIPEA (0.052 g, 0.406 mmol) followed by addition of saturated solution of dimethyl amine in THF (2 mL) at 0° C. and stirred at 0° C. for 3 hours. After complete consumption of starting material, reaction mixture was quenched with water (20 mL), extracted with EtOAc (3×20 mL). Combined organic layer was washed with brine (50 mL), saturated solution of lithium chloride (50 mL), and water (50 mL), dried over sodium sulphate and evaporated in vacuo to get crude. Crude was purified by column chromatography on silica gel (100-200 mesh size). Compound was eluted using 0.6% methanol in DCM to afford white solid (0.050 g, 48%). ¹H-NMR (400 MHz, CDCl₃) δ: 2.94 (s, 3H), 2.97 (s, 3H), 3.61 (d, 1H, J=17.08 Hz), 3.69-3.77 (m, 1H), 4.02 (d, 1H, J=17.04 Hz), 4.11 (d, 4H, J=7.48 Hz), 6.40 (d, 2H, J=8.72 Hz), 7.46 (d, 2H, J=8.68 Hz), 7.63 (s, 2H); LC-MS (m/z): [M+H] 519.80.

Preparation 13

1-{2-chloro-4-[5-(3,4,5-trichloro-phenyl)-5-trifluoromethyl-4,5-dihydroisoxazol-3-yl]-phenyl}-azetidine-3-carboxylic acid methyl ester

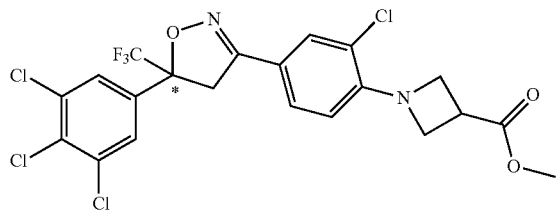 [SMILES: COC(=O)C1CN(c2ccc(C3=NOC(c4cc(Cl)c(Cl)c(Cl)c4)(C(F)(F)F)C3)cc2Cl)C1]

To a stirred solution of 1-[4-(hydroxyimino-methyl)-phenyl]-azetidine-3-carboxylic acid methyl ester (Preparation 10, 0.95 g, 4.059 mmol, 1 eq.) in DMF (10 mL) was added N-chloro succinimide (0.59 g, 4.46 mmol) at room temperature. Resulting reaction mixture was stirred at 45° C. for 30 minutes. After complete consumption of starting material to chloro intermediate, reaction mixture was cooled to room temperature, potassium hydrogen carbonate (0.61 g, 6.089 mmol) was added followed by of 1,2,3-trichloro-5-(1-trifluoromethyl-vinyl)-benzene (1.33 g, 4.87 mmol) at room temperature. Resulting reaction mixture was stirred at room temperature for 18 hours under nitrogen atmosphere. After consumption of chloro intermediate, reaction mixture was quenched with ice cold water (250 mL) and extracted with EtOAc (2×200 mL). Combined organic layer was dried over anhydrous sodium sulphate and concentrated in vacuo to 1 g crude. Crude compound was purified by column chromatography (silica gel, 100-200 mesh) to afford 0.850 g impure product. Impure product was repurified by column chromatography (silica gel, 100-200 mesh) to afford 0.55 g. $^1$H NMR (400 MHz, CDCl$_3$): 3.51-3.55 (m, 1H), 3.60 (d, 1H, J=17.08 Hz), 3.75 (s, 3H), 4.0 (d, 1H, J=17.04 Hz), 4.28 (t, 2H, J=7.2 Hz), 4.36 (t, 2H, J=8.36 Hz), 6.45 (d, 1H, J=8.6 Hz), 7.41 (dd, 1H, J$_1$=1.92 Hz, J$_2$=8.6 Hz), 7.46 (d, 1H, J=1.88 Hz), 7.62 (s, 2H); LC-MS (M+H): =542.50.

Preparation 14

1-{2-chloro-4-[5-(3,4,5-trichloro-phenyl)-5-trifluoromethyl-4,5-dihydro-isoxazol-3-yl]-phenyl}-azetidine-3-carboxylic acid

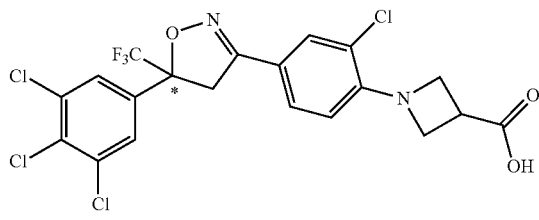 [SMILES: O=C(O)C1CN(c2ccc(C3=NOC(c4cc(Cl)c(Cl)c(Cl)c4)(C(F)(F)F)C3)cc2Cl)C1]

To a stirred suspension of 1-{2-Chloro-4-[5-(3,4,5-trichloro-phenyl)-5-trifluoromethyl-4,5-dihydro-isoxazol-3-yl]-phenyl}-azetidine-3-carboxylic acid methyl ester (Preparation 13, 0.55 g, 1.086 mmol) in THF:MeOH:H$_2$O (1:1:1, 9 mL) was added lithium hydroxide (0.228 g, 5.43 mmol) at room temperature. Resulting reaction mixture was stirred at room temperature for 18 hours. After consumption of starting material, reaction mixture was concentrated in vacuo; acidified with 1N HCl up to pH ~5. Acidified aqueous layer was extracted with ethyl acetate (5×20 mL). Combined organic layer was dried over sodium sulphate and evaporated under reduced pressure and was triturated with n-pentane (25 mL) to afford off white solid (0.4 g, 74%). $^1$H NMR (400 MHz, DMSO-d$_6$) δ: 3.45-3.50 (m, 1H), 4.12-4.16 (m, 2H), 4.26-4.33 (m, 4H), 6.67 (d, 1H, J=9.04 Hz), 7.51-7.53 (m, 2H), 7.81 (s, 2H), 12.75 (bs, 1H); LC-MS (M+H): =528.80.

Example 20

1-{2-chloro-4-[5-(3,4,5-trichloro-phenyl)-5-trifluoromethyl-4,5-dihydro-isoxazol-3-yl]-phenyl}-azetidine-3-carboxylic acid methylamide

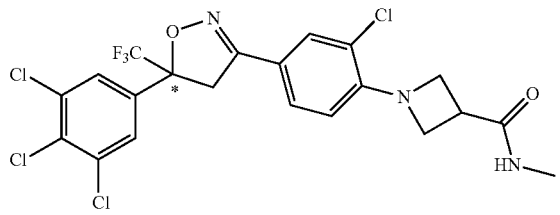 [SMILES: CNC(=O)C1CN(c2ccc(C3=NOC(c4cc(Cl)c(Cl)c(Cl)c4)(C(F)(F)F)C3)cc2Cl)C1]

To a stirred solution of 1-{2-chloro-4-[5-(3,4,5-trichloro-phenyl)-5-trifluoromethyl-4,5-dihydro-isoxazol-3-yl]-phenyl}-azetidine-3-carboxylic acid (Preparation 14, 0.1 g, 0.189 mmol) in DMF (1 mL) was added HATU (0.108 g, 0.284 mmol) HOBt (0.028 g, 0.207 mmol), DIPEA (0.048 g, 0.378 mmol) followed by addition of saturated solution of methyl amine in THF (2 mL) at 0° C. Resulting reaction mixture was stirred at 0° C. for 2 hours and at room temperature for 18 hours. After complete consumption of starting material, reaction mixture was quenched with water (10 mL), extracted with EtOAc (10 mL). Organic layer was washed with saturated solution of lithium chloride (2×20 mL), water (2×20 mL), dried over sodium sulphate and evaporated in vacuo to get brown liquid crude. Crude was purified by column chromatography on silica gel (100-200 mesh size). Compound was eluted using 0.8% methanol in DCM to afford sticky mass, which was crystallized by chloroform: pentane (1:9) to afford white solid (0.026 g, 26%). $^1$H-NMR (400 MHz, CDCl$_3$) δ: 2.85 (d, 3H, J=4.8 Hz), 3.31-3.35 (m, 1H), 3.59 (d, 1H, J=17.1 Hz), 4.00 (d, 1H, J=17 Hz), 4.25-4.33 (m, 4H), 5.63 (bs, 1H), 6.47 (d, 1H, J=8.48 Hz), 7.41 (dd, 1H, J1=8.52 Hz, J2=1.96 Hz), 7.45 (d, 1H, J=1.92 Hz), 7.62 (s, 2H); LC-MS (m/z): [M–H] 537.50.

Example 21

1-{2-chloro-4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide

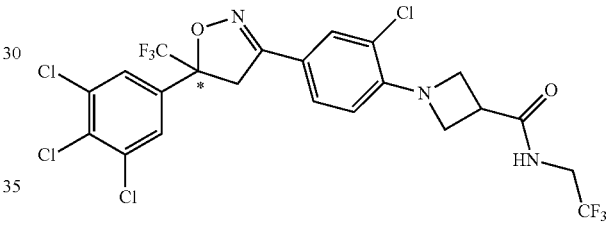

To a stirred solution of 1-{2-chloro-4-[5-(3,4,5-trichloro-phenyl)-5-trifluoromethyl-4,5-dihydro-isoxazol-3-yl]-phenyl}-azetidine-3-carboxylic acid (Preparation 14, 0.1 g, 0.190 mmol) in dry DMF (3 mL) was added EDCl.HCl (0.055 g, 0.280 mmol), DIPEA (0.049 g, 0.380 mmol) and 2,2,2-trifluoro-ethylamine hydrochloride (0.026 g, 0.190 mmol) at 0° C. Resulting reaction mixture was stirred at room temperature for 18 hours under nitrogen atmosphere. After complete consumption of starting material, reaction mixture was quenched with water (50 mL), white solid was precipitated out, and solid was filtered, dried. Solid was purified by preparative TLC to afford off white solid (0.045 g, 41%). $^1$H-NMR (400 MHz, CDCl$_3$) δ: 3.38-3.42 (m, 1H), 3.60 (d, 1H, J=17.08 Hz), 3.93-4.03 (m, 3H), 4.26-4.36 (m, 4H), 5.95 (t, 1H), 6.49 (d, 1H, J=8.52 Hz), 7.42 (dd, 1H, J1=8.56 Hz, J2=1.88 Hz), 7.47 (d, 1H, J=1.84 Hz), 7.62 (s, 2H); LC-MS (m/z): [M–H] 605.40.

Example 22

1-{2-chloro-4-[5-(3,4,5-trichloro-phenyl)-5-trifluoromethyl-4,5-dihydro-isoxazol-3-yl]-phenyl}-azetidine-3-carboxylic acid cyclopropylamide

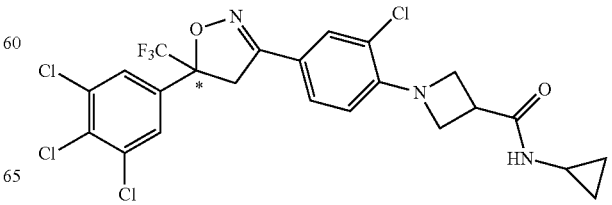

To a stirred solution of 1-{2-chloro-4-[5-(3,4,5-trichloro-phenyl)-5-trifluoromethyl-4,5-dihydro-isoxazol-3-yl]-phenyl}-azetidine-3-carboxylic acid (Preparation 14, 0.1 g, 0.190 mmol) in dry DMF (3 mL) was added EDCl.HCl (0.055 g, 0.280 mmol), DIPEA (0.049 g, 0.380 mmol) and cyclopropyl amine (0.011 g, 0.190 mmol) at 0° C. Resulting reaction mixture was stirred at room temperature for 18 hours under nitrogen atmosphere. After complete consumption of starting material, reaction mixture was quenched with water (10 mL), extracted with EtOAc (10 mL). Organic layer was washed with saturated solution of lithium chloride (3×20 mL), water (2×20 mL), dried over sodium sulphate and evaporated in vacuo to get crude. Crude was purified by column chromatography on silica gel (100-200 mesh size). Compound was eluted using 0.8% methanol in DCM to afford sticky mass, which was crystallized by chloroform:pentane (1:9) to afford off white solid (0.020 g, 20%). $^1$H-NMR (400 MHz, CDCl$_3$) δ: 0.50-0.53 (m, 2H), 0.77-0.82 (m, 2H), 2.72-2.76 (m, 1H), 3.26-3.30 (m, 1H), 3.60 (d, 1H, J=17.12 Hz), 4.00 (d, 1H, J=17 Hz), 4.23-4.33 (m, 4H), 5.72 (bs, 1H), 6.47 (d, 1H, J=8.6 Hz), 7.40 (dd, 1H, J1=8.44 Hz, J2=1.88 Hz), 7.46 (d, 1H, J=1.8 Hz), 7.62 (s, 2H); LC-MS (m/z): [M−H] 563.50.

Example 23

1-{2-chloro-4-[5-(3,4,5-trichloro-phenyl)-5-trifluoromethyl-4,5-dihydro-isoxazol-3-yl]-phenyl}-azetidine-3-carboxylic acid dimethylamide

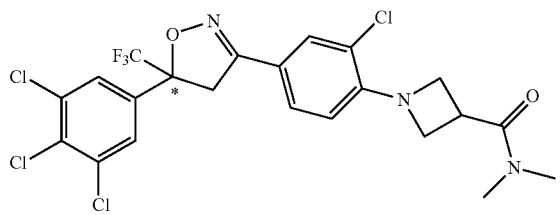 [SMILES: CN(C)C(=O)C1CN(c2ccc(C3=NOC(c4cc(Cl)c(Cl)c(Cl)c4)(C(F)(F)F)C3)cc2Cl)C1]

To a stirred solution of 1-{2-Chloro-4-[5-(3,4,5-trichloro-phenyl)-5-trifluoromethyl-4,5-dihydro-isoxazol-3-yl]-phenyl}-azetidine-3-carboxylic acid (Preparation 14, 0.1 g, 0.189 mmol) in dry DMF (1 mL) was added HATU (0.108 g, 0.284 mmol) HOBt (0.028 g, 0.207 mmol), DIPEA (0.048 g, 0.378 mmol) and saturated solution of dimethyl amine in THF (2 mL) at 0° C. and stirred at 0° C. for 2 hours and at room temperature for 18 hours. After complete consumption of starting material, reaction mixture was quenched with water (15 mL), extracted with EtOAc (10 mL). Organic layer was washed with saturated solution of lithium chloride (2×20 mL), water (2×20 mL), dried over sodium sulphate and evaporated in vacuo to get crude. Crude was purified by column chromatography on silica gel (100-200 mesh size). Further purification by preparative TLC using 5% MeOH in DCM afforded white solid (0.020 g, 19%). $^1$H-NMR (400 MHz, CDCl$_3$) δ: 2.95 (s, 3H), 2.97 (s, 3H), 3.59 (d, 1H, J=17.08 Hz), 3.67-3.71 (m, 1H), 4.00 (d, 1H, J=17.04 Hz), 4.29-4.38 (m, 4H), 6.48 (d, 1H, J=8.6 Hz), 7.40 (dd, 1H, J1=8.48 Hz, J2=2 Hz), 7.45 (d, 1H, J=1.92 Hz), 7.62 (s, 2H); LC-MS (m/z): [M+H] 554.10.

Preparation 15

2-(trimethylsilyl)ethyl (3-fluoro-3-(4-(5-(3,4,5-trichlorophenyl)-5-(trifluoromethyl)-4,5-dihydroisoxazol-3-yl)phenyl)cyclobutyl)carbamate

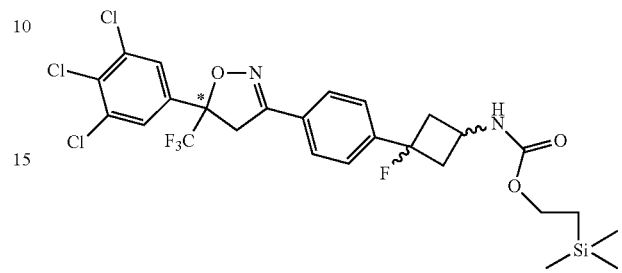

Diphenyl phosphoryl azide (93 μL, 0.43 mmol) is added to 3-fluoro-3-(4-(5-(3,4,5-trichlorophenyl)-5-(trifluoromethyl)-4,5-dihydroisoxazol-3-yl)phenyl)cyclobutanecarboxylic acid (from Preparation 6 and Preparation 7, 200 mg, 0.39 mmol) along with triethylamine (66 μL, 0.47 mmol) and 2-trimethylsilylethanol (60 μL, 0.41 mmol) in THF (4.0 mL) and the mixture heated to 64° C. for 16 hours. After cooling to room temperature the mixture is partitioned between water (10 mL) and EtOAc (10 mL). The organics are separated, dried over MgSO$_4$, filtered and evaporated to give a yellow oil, which is further purified using on regular silica from neat heptane to neat EtOAc to give the title compound (130 mg): $^1$H NMR (CDCl$_3$) δ: 7.64-7.60 (4H, m), 7.46-7.44 (2H, m), 4.83 (1H, m), 4.14-4.09 (2H, m), 4.05 (2H, d), 3.64 (2H, d), 2.97-2.87 (2H, m), 2.66-2.56 (2H, m), 1.26-1.20- (1H, m), 0.96-0.91 (2H, m), 0.00 (9H, s).

Preparation 16

3-fluoro-3-(4-(5-(3,4,5-trichlorophenyl)-5-(trifluoromethyl)-4,5-dihydroisoxazol-3-yl)phenyl)cyclobutanamine

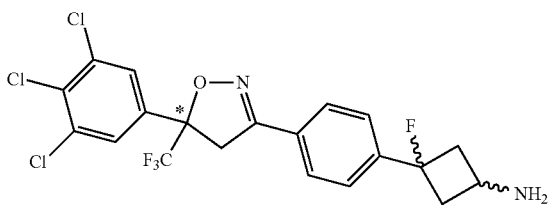 [SMILES: NC1CC(F)(c2ccc(C3=NOC(c4cc(Cl)c(Cl)c(Cl)c4)(C(F)(F)F)C3)cc2)C1]

1.0 M TBAF in THF (576 μL, 0.576 mmol) is added to a mixture of 2-(trimethylsilyl)ethyl (3-fluoro-3-(4-(5-(3,4,5-trichlorophenyl)-5-(trifluoromethyl)-4,5-dihydroisoxazol-3-yl)phenyl)cyclobutyl)carbamate (Preparation 15, 120.0 mg, 0.19 mmol) in THF (1.9 mL). After stirring overnight, the reaction mixture is partitioned between EtOAc (5 mL) and brine (5 mL), the organics were separated, dried over MgSO$_4$ and filtered to give an oil which was further purified using regular silica eluting from neat heptane to neat EtOAc to give the title compound (100 mg): m/z (Cl) 480.

Example 24

N-(3-fluoro-3-(4-(5-(3,4,5-trichlorophenyl)-5-(trifluoromethyl)-4,5-dihydroisoxazol-3-yl)phenyl)cyclobutyl)cyclopropanecarboxamide

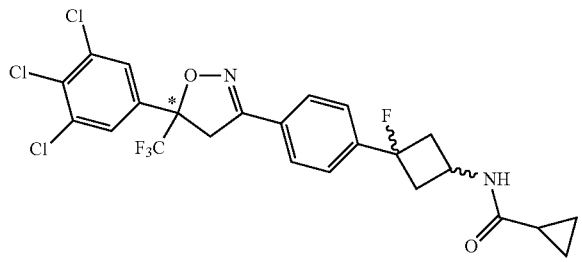 [SMILES: O=C(NC1CC(F)(c2ccc(C3=NOC(c4cc(Cl)c(Cl)c(Cl)c4)(C(F)(F)F)C3)cc2)C1)C1CC1]

Cyclopropylcarbonylchloride (14.1 µL, 0.10 mmol) is added to 3-fluoro-3-(4-(5-(3,4,5-trichlorophenyl)-5-(trifluoromethyl)-4,5-dihydroisoxazol-3-yl)phenyl)cyclobutanamine (Preparation 16, 50.0 mg, 0.10 mmol) in DMF (1.5 mL) along with DIPEA (5.4 µL, 0.31 mmol) and DMAP (1.2 mg, 0.01 mmol). The reaction mixture is stirred for three days at room temperature. The mixture is partitioned between brine (5 mL) and EtOAc (5 mL). The organics are separated, dried over MgSO$_4$, filtered and evaporated to give a residue, which is purified on regular silica eluting from neat DCM to 15% MeOH/DCM to give the title compound (22 mg): $^1$H NMR (DMSO-d$_6$) δ: 8.83 (1H, d), 7.88 (2H, s), 7.79 (2H, d), 7.58 (2H, d), 4.61-4.53 (1H, m), 4.42-4.30 (2H, m), 2.89-2.78 (2H, m), 2.65-2.55 (2H, m), 1.50-1.44 (1H, m), 0.71-0.61 (4H, m); m/z (Cl) 548.

Example 25

N-(3-fluoro-3-(4-(5-(3,4,5-trichlorophenyl)-5-(trifluoromethyl)-4,5-dihydroisoxazol-3-yl)phenyl)cyclobutyl)-2-(methylsulfonyl)acetamide

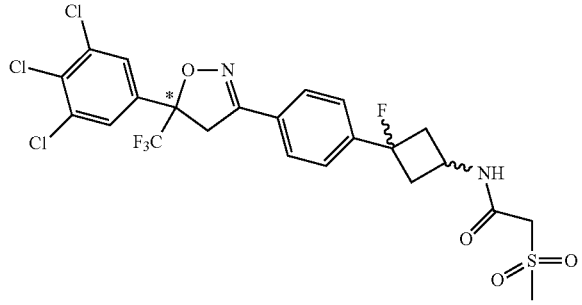 [SMILES: CS(=O)(=O)CC(=O)NC1CC(F)(c2ccc(C3=NOC(c4cc(Cl)c(Cl)c(Cl)c4)(C(F)(F)F)C3)cc2)C1]

2-(methylsulfonyl)acetic acid (22 mg, 0.16 mmol) was added to 3-fluoro-3-(4-(5-(3,4,5-trichlorophenyl)-5-(trifluoromethyl)-4,5-dihydroisoxazol-3-yl)phenyl)cyclobutanamine (Preparation 16, 50.0 mg, 0.10 mmol) in DMF (1.5 mL) along with DIPEA (54 µL, 0.31 mmol) and HATU (61 mg, 0.16 mmol). The mixture is stirred for 3 days at room temperature. The reaction mixture is partitioned between brine (5 mL) and EtOAc (5 mL). The organics are separated, dried over MgSO$_4$, filtered and evaporated to give a residue, which is purified on regular silica eluting from neat DCM to 15% MeOH/DCM to give the title compound (20 mg): $^1$H NMR (DMSO-d$_6$) δ: 8.83 (1H, d), 7.85 (2H, s), 7.79 (2H, d), 7.58 (2H, d), 4.60-4.51 (1H, m), 4.42-4.30 (2H, m), 4.04 (2H, s), 3.12 (3H, s), 2.96-2.86 (2H, m), 2.65-2.54 (2H, m); m/z (Cl) 602.

Biological Assays

The biological activity of the compounds of the present invention can be tested against fleas, horn flies, soft tick, and hard tick larvae using the test methods described below.

Mosquito (*Aedes aegypti*) Larval Assay

Formula (1) compounds were dissolved in DMSO and water. Five instar mosquito larvae were added to the solution and observed for death or paralysis following a 24 hour incubation period at 22° C. Endpoint data was recorded as Minimum Efficacious Dose (MED) in µM. In this assay, Examples 1-4 and 7-25 had an MED of ≤100 µM.

Flea (*Ctenocephalides felis*) Membrane Feed Assay-Adult

Formula (1) compounds can be dissolved in DMSO and aliquots added to citrated bovine blood in a membrane covered Petri dish pre-warmed to 37° C. Feeding tubes containing approximately 30-35 adult fleas can be placed onto the Petri dishes. The fleas are then allowed to feed for approximately 2 hours. Fleas are then observed for knockdown and/or death at approximately 2 and 24 hours. Endpoint data can be recorded as an efficacious dose 80% (ED$^{80}$) or lethal dose 80% (LD$^{80}$) in µg/mL. In this assay, Examples 1-4, 8-15, and 24-25 had a LD$^{80}$ of ≤30 µg/mL. Examples 5, 8, and 12 had an LD$^{80}$ of ≤3 µg/mL.

We claim:
1. A compound of Formula (1)

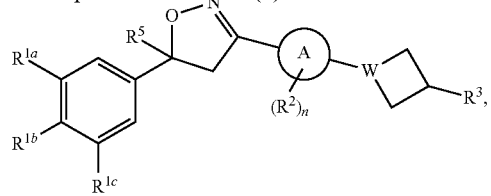

wherein

A is phenyl, naphthyl, or heteroaryl where said heteroaryl contains 1 to 4 heteroatoms each independently selected from N, O and S;

W is N or CR$^c$;

R$^{1a}$, R$^{1b}$, and R$^{1c}$ are each independently hydrogen, halo, cyano, nitro, C$_1$-C$_6$alkyl, C$_1$-C$_6$haloalkyl, C$_1$-C$_6$alkoxy, C$_0$-C$_3$alkylC$_3$-C$_6$ cycloalkyl, C$_1$-C$_6$haloalkoxy, —C(O)NH$_2$, —SF$_5$, or —S(O)$_p$R;

R$^2$ is halo, cyano, C$_1$-C$_6$alkyl, nitro, hydroxyl, —C(O)NH$_2$, C$_2$-C$_6$alkenyl, C$_2$-C$_6$alkynyl, or —OR;

R$^3$ is —C(X)NR$^a$R$^4$ or —NR$^a$C(X)R$^4$, where X is O, S, or NR$^6$;

R$^4$ is hydrogen, C$_1$-C$_6$alkyl, C$_0$-C$_3$alkylC$_3$-C$_6$cycloalkyl, C$_0$-C$_3$alkylphenyl, C$_0$-C$_3$alkylheteroaryl, or C$_0$-C$_3$alkylheterocycle; wherein said phenyl, heteroaryl, and heterocycle moieties are optionally substituted with one or more substituents selected from cyano, halo, hydroxyl, C$_1$-C$_6$alkoxy, C$_1$-C$_6$alkyl, and C$_1$-C$_6$haloalkoxy;

R$^5$ is cyano, C$_1$-C$_6$alkyl, C$_1$-C$_6$haloalkyl, —C(O)NH$_2$, C$_2$-C$_6$alkenyl, C$_2$-C$_6$alkynyl, C$_2$-C$_6$haloalkenyl, or C$_2$-C$_6$haloalkynyl;

R$^6$ is hydrogen, C$_1$-C$_6$alkyl, hydroxyl, cyano, nitro, S(O)$_p$ R, or C$_1$-C$_6$alkoxy;

R and R' are each independently C$_1$-C$_6$alkyl or C$_3$-C$_6$cycloalkyl;

R$^a$ is hydrogen, C$_1$-C$_6$alkyl, C$_0$-C$_3$alkylC$_3$-C$_6$cycloalkyl, C(O)R$^4$, or C(O)OR; wherein the alkyl and alkylcycloalkyl moiety is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each of which may be optionally substituted with at least one halo;

$R^c$ is halo, hydroxyl, cyano, $C_1$-$C_5$alkyl, or $C_1$-$C_5$ haloalkyl;

each of R, $R^2$, $R^3$, and $R^4$ $C_1$-$C_6$alkyl or $C_0$-$C_3$alkyl$C_3$-$C_6$cycloalkyl can be optionally and independently substituted by one or more substituents selected from cyano, halo, hydroxyl, oxo, $C_1$-$C_6$alkoxy, $C_1$-$C_6$alkyl, hydroxy$C_1$-$C_6$alkyl-, and $C_1$-$C_6$haloalkoxy, and wherein $R^4$ $C_1$-$C_6$alkyl and $C_0$-$C_3$alkyl$C_3$-$C_6$cycloalkyl can be further optionally substituted by —S(O)$_p$R$^b$, —NR$^a$R$^b$, —NR$^a$C(O)R$^b$, —SC(O)R', or —C(O)NR$^a$R$^b$;

n is the integer 0, 1, or 2, and when n is 2, each $R^2$ may be identical or different from each other; and p is the integer 0, 1, or 2;

stereoisomers thereof, geometric isomers thereof, and veterinarily acceptable salts thereof.

2. The compound of claim 1 having Formula (2) or (6)

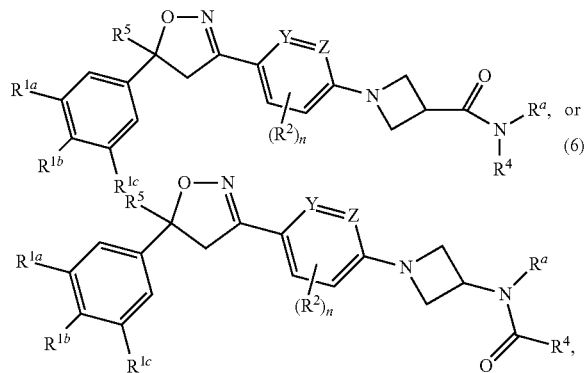

wherein
Y and Z are each independently C or N, and Y and Z are not both N;
stereoisomers thereof, and veterinarily acceptable salts thereof.

3. The compound of claim 2 wherein
$R^{1a}$, $R^{1b}$, and $R^{1c}$ are each independently hydrogen, halo, cyano, $C_1$-$C_6$alkyl, or $C_1$-$C_6$haloalkyl;
$R^2$ is halo, cyano, $C_1$-$C_6$alkyl, or hydroxyl;
$R^5$ is trifluoromethyl; and
$R^a$ is hydrogen or $C_1$-$C_6$alkyl optionally substituted by cyano or at least one halo substituent;
stereoisomers thereof, and veterinarily acceptable salts thereof.

4. The compound of claim 3 wherein
$R^{1a}$, $R^{1b}$, and $R^{1c}$ are each independently hydrogen, chloro, fluoro, bromo, cyano, or trifluoromethyl;
$R^2$ is halo, cyano, methyl, or hydroxyl;
$R^a$ is hydrogen, methyl, or ethyl; and
$R^4$ is $C_1$-$C_6$alkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle; wherein said phenyl, heteroaryl, and heterocycle moieties are optionally substituted with one or more substituents selected from cyano, halo, hydroxyl, or $C_1$-$C_6$alkyl; and wherein the $R^4$ $C_1$-$C_6$alkyl or $C_0$-$C_3$alkyl$C_3$-$C_6$cycloalkyl can be optionally and independently substituted by one or more substituents selected from cyano, halo, hydroxyl, $C_1$-$C_6$alkoxy, $C_1$-$C_6$alkyl, —S(O)$_p$R$^b$, —C(O)NR$^a$R$^b$, —NR$^a$C(O)R$^b$, and hydroxy$C_1$-$C_6$alkyl-;
stereoisomers thereof, and veterinarily acceptable salts thereof.

5. The compound of claim 4 wherein
Y and Z are both carbon;
$R^{1a}$, $R^{1b}$, and $R^{1c}$ are each independently hydrogen, chloro, fluoro, bromo, or trifluoromethyl;
$R^a$ is hydrogen or methyl;
$R^4$ is $C_1$-$C_6$alkyl or $C_0$-$C_3$alkyl$C_3$-$C_6$cycloalkyl, each optionally substituted by one or more substituents selected from halo, hydroxyl, $C_1$-$C_6$alkyl, hydroxy$C_1$-$C_6$alkyl-, —C(O)NR$^a$R$^b$, —NR$^a$C(O)R$^b$, and —S(O)$_p$R$^b$; and
n is the integer 0;
stereoisomers thereof, and veterinarily acceptable salts thereof.

6. The compound of claim 1 having Formula (7) or (11)

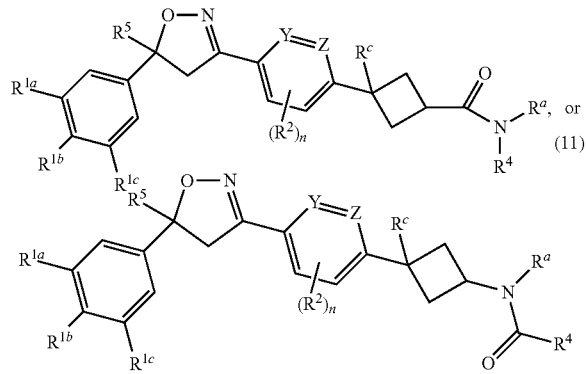

wherein
Y and Z are each independently C or N, and Y and Z are not both N,
stereoisomers thereof, geometric isomers thereof, and veterinarily acceptable salts thereof.

7. The compound of claim 6 wherein
$R^{1a}$, $R^{1b}$, and $R^{1c}$ are each independently hydrogen, halo, cyano, $C_1$-$C_6$alkyl, or $C_1$-$C_6$haloalkyl;
$R^2$ is halo, cyano, $C_1$-$C_6$alkyl, or hydroxyl;
$R^5$ is trifluoromethyl;
$R^a$ is hydrogen or $C_1$-$C_6$alkyl optionally substituted by cyano or at least one halo substituent; and
$R^c$ is halo, hydroxyl, cyano, or $C_1$-$C_5$ haloalkyl;
stereoisomers thereof, geometric isomers thereof, and veterinarily acceptable salts thereof.

8. The compound of claim 7 wherein
$R^{1a}$, $R^{1b}$, and $R^{1c}$ are each independently hydrogen, chloro, fluoro, bromo, cyano, or trifluoromethyl;
$R^2$ is halo, cyano, methyl, or hydroxyl;
$R^a$ is hydrogen, methyl, or ethyl;
$R^c$ is halo, hydroxyl, or trifluoromethyl; and
$R^4$ is $C_1$-$C_6$alkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle; wherein said phenyl, heteroaryl, and heterocycle moieties are optionally substituted with one or more substituents selected from cyano, halo, hydroxyl, or $C_1$-$C_6$alkyl; and wherein the $R^4$ $C_1$-$C_6$alkyl or $C_0$-$C_3$alkyl$C_3$-$C_6$cycloalkyl can be optionally and independently substituted by one or more substituents selected from cyano, halo, hydroxyl, $C_1$-$C_6$alkoxy, $C_1$-$C_6$alkyl, —S(O)$_p$R$^b$, —C(O)NR$^a$R$^b$, —NR$^a$C(O)R$^b$, and hydroxy$C_1$-$C_6$alkyl-;

stereoisomers thereof, geometric isomers thereof, and veterinarily acceptable salts thereof.

9. The compound of claim 8 wherein
Y and Z are both carbon;
$R^{1a}$, $R^{1b}$, and $R^{1c}$ are each independently hydrogen, chloro, fluoro, bromo, or trifluoromethyl;
$R^a$ is hydrogen or methyl;
$R^c$ is fluoro, chloro, hydroxyl, or trifluoromethyl;
$R^4$ is $C_1$-$C_6$alkyl or $C_0$-$C_3$alkyl$C_3$-$C_6$cycloalkyl, each optionally substituted by one or more substituents selected from halo, hydroxyl, $C_1$-$C_6$alkyl, hydroxy$C_1$-$C_6$alkyl-, —C(O)NR$^a$R$^b$, —NR$^a$C(O)R$^b$, and —S(O)$_p$R$^b$; and
n is the integer 0;
stereoisomers thereof, geometric isomers thereof, and veterinarily acceptable salts thereof.

10. A compound selected from the group consisting of
3-hydroxy-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;
3-hydroxy-3-{4-[5-(3,4,5-trichloro-phenyl)-5-trifluoromethyl-4,5-dihydro-isoxazol-3-yl]-phenyl}-cyclobutanecarboxylic acid cyclopropylamide;
3-hydroxy-3-{4-[5-(3,4,5-trichloro-phenyl)-5-trifluoromethyl-4,5-dihydro-isoxazol-3-yl]-phenyl}-cyclobutanecarboxylic acid methylamide;
3-hydroxy-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid cyclopropylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;
3-fluoro-3-{4-[5-(3,4,5-trichloro-phenyl)-5-trifluoromethyl-4,5-dihydro-isoxazol-3-yl]-phenyl}-cyclobutanecarboxylic acid (2,2,2-trifluoro-ethyl)-amide;
3-fluoro-3-{4-[5-(3,4,5-trichloro-phenyl)-5-trifluoromethyl-4,5-dihydro-isoxazol-3-yl]-phenyl}-cyclobutanecarboxylic acid methylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid methylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid dimethylamide;
3-fluoro-3-{4-[5-(3,4,5-trichloro-phenyl)-5-trifluoromethyl-4,5-dihydro-isoxazol-3-yl]-phenyl}-cyclobutanecarboxylic acid;
3-fluoro-3-{4-[5-(3,4,5-trichloro-phenyl)-5-trifluoromethyl-4,5-dihydro-isoxazol-3-yl]-phenyl}-cyclobutanecarboxylic acid ethylamide;
3-fluoro-N-(2-oxo-2-((2,2,2-trifluoroethyl)amino)ethyl)-3-(4-(5-(3,4,5-trichlorophenyl)-5-(trifluoromethyl)-4,5-dihydroisoxazol-3-yl)phenyl)cyclobutanecarboxamide;
1-{4-[5-(3,4,5-trichloro-phenyl)-5-trifluoromethyl-4,5-dihydro-isoxazol-3-yl]-phenyl}-azetidine-3-carboxylic acid cyclopropylamide;
1-{4-[5-(3,4,5-trichloro-phenyl)-5-trifluoromethyl-4,5-dihydro-isoxazol-3-yl]-phenyl}-azetidine-3-carboxylic acid methylamide;
1-{4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)amide;
1-{4-[5-(3,4,5-trichloro-phenyl)-5-trifluoromethyl-4,5-dihydro-isoxazol-3-yl]-phenyl}azetidine-3-carboxylic acid dimethylamide;
1-{2-chloro-4-[5-(3,4,5-trichloro-phenyl)-5-trifluoromethyl-4,5-dihydro-isoxazol-3-yl]-phenyl}-azetidine-3-carboxylic acid methylamide;
1-{2-chloro-4-[5-(3,4,5-trichloro-phenyl)-5-trifluoromethyl-4,5-dihydro-isoxazol-3-yl]-phenyl}-azetidine-3-carboxylic acid (2,2,2-trifluoro-ethyl)-amide;
1-{2-chloro-4-[5-(3,4,5-trichloro-phenyl)-5-trifluoromethyl-4,5-dihydro-isoxazol-3-yl]-phenyl}-azetidine-3-carboxylic acid cyclopropylamide;
1-{2-chloro-4-[5-(3,4,5-trichloro-phenyl)-5-trifluoromethyl-4,5-dihydro-isoxazol-3-yl]-phenyl}-azetidine-3-carboxylic acid dimethylamide;
N-(3-fluoro-3-(4-(5-(3,4,5-trichlorophenyl)-5-(trifluoromethyl)-4,5-dihydroisoxazol-3-yl)phenyl)cyclobutyl)cyclopropanecarboxamide; and
N-(3-fluoro-3-(4-(5-(3,4,5-trichlorophenyl)-5-(trifluoromethyl)-4,5-dihydroisoxazol-3-yl)phenyl)cyclobutyl)-2-(methylsulfonyl)acetamide;
stereoisomers thereof, geometric isomers thereof, and veterinarily acceptable salts thereof.

11. A pharmaceutical or veterinary composition comprising a therapeutic amount of a compound of Formula (1)

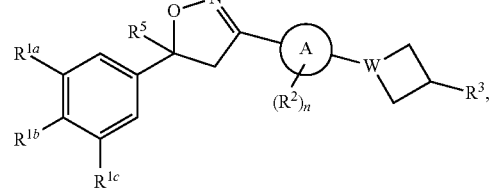

wherein
A is phenyl, naphthyl, or heteroaryl where said heteroaryl contains 1 to 4 heteroatoms each independently selected from N, O and S;
W is N or CR$^c$;
$R^{1a}$, $R^{1b}$, and $R^{1c}$ are each independently hydrogen, halo, cyano, nitro, $C_1$-$C_6$alkyl, $C_1$-$C_6$haloalkyl, $C_1$-$C_6$alkoxy, $C_0$-$C_3$alkyl$C_3$-$C_6$cycloalkyl, $C_1$-$C_6$haloalkoxy, —C(O)NH$_2$, —SF$_5$, or —S(O)$_p$R;
$R^2$ is halo, cyano, $C_1$-$C_6$alkyl, nitro, hydroxyl, —C(O)NH$_2$, $C_2$-$C_6$alkenyl, $C_2$-$C_6$alkynyl, or —OR;
$R^3$ is —C(X)NR$^a$R$^4$ or —NR$^a$C(X)R$^4$, where X is O, S, or NR$^6$;
$R^4$ is hydrogen, $C_1$-$C_6$alkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle; wherein said phenyl, heteroaryl, and heterocycle moieties are optionally substituted with one or more substituents selected from cyano, halo, hydroxyl, $C_1$-$C_6$alkoxy, $C_1$-$C_6$alkyl, and $C_1$-$C_6$haloalkoxy;
$R^5$ is cyano, $C_1$-$C_6$alkyl, $C_1$-$C_6$haloalkyl, —C(O)NH$_2$, $C_2$-$C_6$alkenyl, $C_2$-$C_6$alkynyl, $C_2$-$C_6$haloalkenyl, or $C_2$-$C_6$haloalkynyl;
$R^6$ is hydrogen, $C_1$-$C_6$alkyl, hydroxyl, cyano, nitro, S(O)$_p$R, or $C_1$-$C_6$alkoxy;
R and R' are each independently $C_1$-$C_6$alkyl or $C_3$-$C_6$cycloalkyl;

$R^a$ is hydrogen, $C_1$-$C_6$alkyl, $C_0$-$C_3$alkyl$C_3$-$C_6$cycloalkyl, $C(O)R^4$, or $C(O)OR$; wherein the alkyl and alkylcycloalkyl moiety is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each of which may be optionally substituted with at least one halo;

$R^c$ is halo, hydroxyl, cyano, $C_1$-$C_5$alkyl, or $C_1$-$C_5$ haloalkyl;

each of R, $R^2$, $R^3$, and $R^4$ $C_1$-$C_6$alkyl or $C_0$-$C_3$alkyl$C_3$-$C_6$cycloalkyl can be optionally and independently substituted by one or more substituents selected from cyano, halo, hydroxyl, oxo, $C_1$-$C_6$alkoxy, $C_1$-$C_6$alkyl, hydroxy$C_1$-$C_6$alkyl-, and $C_1$-$C_6$haloalkoxy, and wherein $R^4$ $C_1$-$C_6$alkyl and $C_0$-$C_3$alkyl$C_3$-$C_6$cycloalkyl can be further optionally substituted by $—S(O)_pR^b$, $—NR^aR^b$, $—NR^aC(O)R^b$, $—SC(O)R'$, or $—C(O)NR^aR^b$;

n is the integer 0, 1, or 2, and when n is 2, each $R^2$ may be identical or different from each other; and p is the integer 0, 1, or 2;

stereoisomers thereof, geometric isomers thereof, and veterinarily acceptable salts thereof.

12. The pharmaceutical or veterinary composition of claim 11 further comprising a veterinarily acceptable excipient, diluent, or carrier.

13. The pharmaceutical or veterinary composition of claim 12 further comprising at least one additional veterinary agent, wherein said additional veterinary agent is selected from the group consisting of avermectin, selamectin, doramectin, moxidectin, eprinomectin, milbemycin, milbemycin oxime, pyriproxyfen, DEET, demiditraz, amitraz, fipronil, methoprene, hydroprene, metaflumizone, permethrin, pyrethrin, and spinosad, or mixtures thereof.

14. A method for the treatment of an animal with a parasitic infection or infestation comprising administering to said animal in need thereof an effective amount of a compound of Formula (1)

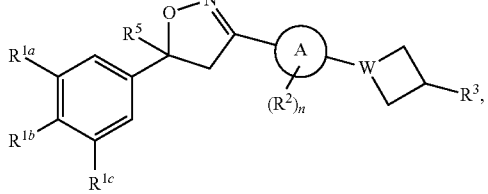

wherein

A is phenyl, naphthyl, or heteroaryl where said heteroaryl contains 1 to 4 heteroatoms each independently selected from N, O and S;

W is N or $CR^c$;

$R^{1a}$, $R^{1b}$, and $R^{1c}$ are each independently hydrogen, halo, cyano, nitro, $C_1$-$C_6$alkyl, $C_1$-$C_6$haloalkyl, $C_1$-$C_6$alkoxy, $C_0$-$C_3$alkyl$C_3$-$C_6$ cycloalkyl, $C_1$-$C_6$haloalkoxy, $—C(O)NH_2$, $—SF_5$, or $—S(O)_pR$;

$R^2$ is halo, cyano, $C_1$-$C_6$alkyl, nitro, hydroxyl, $—C(O)NH_2$, $C_2$-$C_6$alkenyl, $C_2$-$C_6$alkynyl, or $—OR$;

$R^3$ is $—C(X)NR^aR^4$ or $—NR^aC(X)R^4$, where X is O, S, or $NR^6$;

$R^4$ is hydrogen, $C_1$-$C_6$alkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle; wherein said phenyl, heteroaryl, and heterocycle moieties are optionally substituted with one or more substituents selected from cyano, halo, hydroxyl, $C_1$-$C_6$alkoxy, $C_1$-$C_6$alkyl, and $C_1$-$C_6$haloalkoxy;

$R^5$ is cyano, $C_1$-$C_6$alkyl, $C_1$-$C_6$haloalkyl, $—C(O)NH_2$, $C_2$-$C_6$alkenyl, $C_2$-$C_6$alkynyl, $C_2$-$C_6$haloalkenyl, or $C_2$-$C_6$haloalkynyl;

$R^6$ is hydrogen, $C_1$-$C_6$alkyl, hydroxyl, cyano, nitro, $S(O)_p R$, or $C_1$-$C_6$alkoxy;

R and R' are each independently $C_1$-$C_6$alkyl or $C_3$-$C_6$cycloalkyl;

$R^a$ is hydrogen, $C_1$-$C_6$alkyl, $C_0$-$C_3$alkyl$C_3$-$C_6$cycloalkyl, $C(O)R^4$, or $C(O)OR$; wherein the alkyl and alkylcycloalkyl moiety is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each of which may be optionally substituted with at least one halo;

$R^c$ is halo, hydroxyl, cyano, $C_1$-$C_5$alkyl, or $C_1$-$C_5$ haloalkyl;

each of R, $R^2$, $R^3$, and $R^4$ $C_1$-$C_6$alkyl or $C_0$-$C_3$alkyl$C_3$-$C_6$cycloalkyl can be optionally and independently substituted by one or more substituents selected from cyano, halo, hydroxyl, oxo, $C_1$-$C_6$alkoxy, $C_1$-$C_6$alkyl, hydroxy$C_1$-$C_6$alkyl-, and $C_1$-$C_6$haloalkoxy, and wherein $R^4$ $C_1$-$C_6$alkyl and $C_0$-$C_3$alkyl$C_3$-$C_6$cycloalkyl can be further optionally substituted by $—S(O)_pR^b$, $—NR^aR^b$, $—NR^aC(O)R^b$, $—SC(O)R'$, or $—C(O)NR^aR^b$;

n is the integer 0, 1, or 2, and when n is 2, each $R^2$ may be identical or different from each other; and p is the integer 0, 1, or 2;

stereoisomers thereof, geometric isomers thereof, and veterinarily acceptable salts thereof.

15. The method of claim 14 wherein the compound is administered topically, orally, or subcutaneously and wherein said animal is a companion animal or livestock.

* * * * *